United States Patent
Kevil et al.

(10) Patent No.: US 10,697,960 B2
(45) Date of Patent: *Jun. 30, 2020

(54) CXCR4 AND ROBO1 EXPRESSION AS MARKERS FOR AUTOIMMUNE DIABETES

(71) Applicants: Christopher Kevil, Shreveport, LA (US); Robert McVie, Shreveport, LA (US); John Glawe, Benton, LA (US)

(72) Inventors: Christopher Kevil, Shreveport, LA (US); Robert McVie, Shreveport, LA (US); John Glawe, Benton, LA (US)

(73) Assignee: BOARD OF SUPERVISORS OR LOUISANA STATE UNIVERSITY AND AGRICULTURAL AND MECHANICAL COLLEGE, Shreveport, LA (US)

( * ) Notice: Subject to any disclaimer, the term of this patent is extended or adjusted under 35 U.S.C. 154(b) by 110 days.

This patent is subject to a terminal disclaimer.

(21) Appl. No.: 14/950,202

(22) Filed: Nov. 24, 2015

(65) Prior Publication Data

US 2016/0146807 A1 May 26, 2016

Related U.S. Application Data

(62) Division of application No. 14/024,751, filed on Sep. 12, 2013, now Pat. No. 9,234,886.

(60) Provisional application No. 61/700,429, filed on Sep. 13, 2012.

(51) Int. Cl.

| | |
|---|---|
| *G01N 33/564* | (2006.01) |
| *C12Q 1/68* | (2018.01) |
| *G01N 33/566* | (2006.01) |
| *A61K 38/19* | (2006.01) |
| *G01N 33/50* | (2006.01) |
| *C12Q 1/6883* | (2018.01) |
| *A61K 49/00* | (2006.01) |

(52) U.S. Cl.
CPC ......... *G01N 33/564* (2013.01); *A61K 38/195* (2013.01); *C12Q 1/6883* (2013.01); *G01N 33/5091* (2013.01); *G01N 33/566* (2013.01); *A61K 49/0004* (2013.01); *C12Q 2600/158* (2013.01); *G01N 2333/7158* (2013.01); *G01N 2800/042* (2013.01)

(58) Field of Classification Search
CPC .............. A61K 38/195; A61K 49/0004; C12Q 1/6883; C12Q 2600/158; G01N 2333/7158; G01N 2800/042; G01N 33/5091; G01N 33/564; G01N 33/566
See application file for complete search history.

(56) References Cited

U.S. PATENT DOCUMENTS

2010/0298214 A1  11/2010  Leng et al.

OTHER PUBLICATIONS

UniProt Protein Database, Human SDF-1, protein accession No. P48061, accessed Jun. 30, 2014.
Weigmann, Benno et al., Immunotherapy in Autoimmune Type 1 Diabetes, Rev Diabet Stud, 2012, 9:68-81.
Yano, Tatsuya et al., Stromal Cell-Derived Factor-1 (SDF-1)/CXCL12 Attenuates Diabetes in Mice and Promotes Pancreatic-Cell Survival by Activation of the Prosurvival Kinase Akt, Diabetes, vol. 56, Dec. 2007.
UniProt Protein Database, ROBO1, accession No. Q9Y6N7 (ROBO1_HUMAN), accessed on Aug. 19, 2014.
UniProt Protein Database, CXCR4, accession No. P61073 (CXCR4_HUMAN), accessed on Aug. 19, 2014.
Aboumrad, E. et al., "The CXCR4/CXCL12 (SD-1) Signaling Pathway Protects Non-Obese Diabetic Mouse From Autoimmune Diabetes," Clinal and Experimental Immunology, vol. 148, pp. 432-439 (2007).
Prasad, A. et al., "The Protein-Mediated Inhibition of CXCR4-Induced Chemotactic and Chemoinvasive Signaling Pathways in Breast Cancer Cells," J Biol Chem, vol. 5, No. 279(10), pp. 9115-9124 (2004).
Sharp, C. et al., "Stromal Cell-Derived Factor-1/CXCL12 Stimulates Chemorepulsion of NOD/LtJ T Cell Adhesion to Islet Microvascular Endothelium," Diabetes, vol. 57, pp. 102-112 (2008).
K. Fang et al., "Temporal genomewide expression profiling of DSS colitis reveals novel inflammatory and angiogenesis genes similar to ulcerative colitis", Physiological genomics 43: 43-56 (2011).
Tudan et al., "C-terminal cyclization of an SDF-1 small peptide analogue dramatically increases receptor affinity and activation of CXCR4 receptor," J. Med. Chem., vol. 45, pp. 2024-2031 (2002).
J. Glawe et al., "Genetic deficiency of Itgb2 or ItgaL prevents autoimmune diabetes through distinctly different mechanisms in NOD/LtJ mice", Diabetes 58: 1292-1301 (2009).
K Li, et al., "Small peptide analogue of SDF-1a supports survival of cord blood CD34+ cells in synergy with other cytokines and enhances their ex vivo expansion and engraftment into nonobese diabetic/severe combined immunodeficient mice", Stem Cells, vol. 24, pp. 56-64 (2006).
R. Zhong et al., "Small peptide analogs to stromal derived factor 1 enhance chemotactic migration of human and mouse hematopoietic cells", Experimental Hematology, vol. 32, pp. 470-475 (2004).
A. Faber et al., "The many facets of SDF-1, CXCR4 agonists and antagonists on hematopoietic progenitor cells", Journal of Biomedicine and Biotechnology, Article ID 26065; doi: 10.1155/200726065 (2007).

*Primary Examiner* — James H Alstrum-Acevedo
*Assistant Examiner* — Erinne R Dabkowski
(74) *Attorney, Agent, or Firm* — Davis & Bujold PLLC; Charles G. Holoubek

(57) ABSTRACT

CXCR4 and ROBO-1 are biomarkers associated with type 1 diabetes. Expression of CXCR4 and ROBO-1 in peripheral CD3 T cells is substantially higher in patients with autoimmune diabetes (type 1 diabetes) than in non-diabetic patients. Therapies are disclosed for reducing the progression of type 1 diabetes, and to reduce the risk of developing type 1 diabetes in patients who are at risk of developing type 1 diabetes.

18 Claims, 6 Drawing Sheets

Specification includes a Sequence Listing.

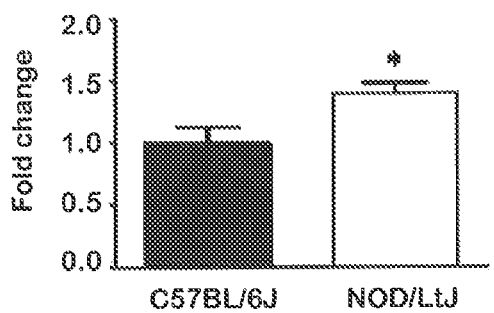
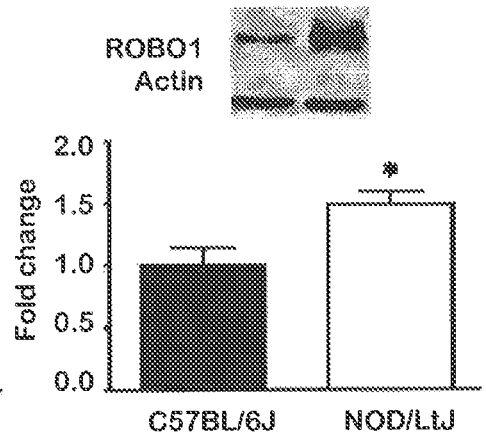
Fig. 1A  Fig. 1B
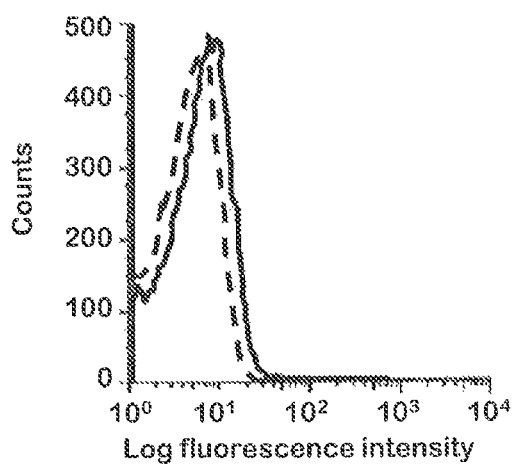
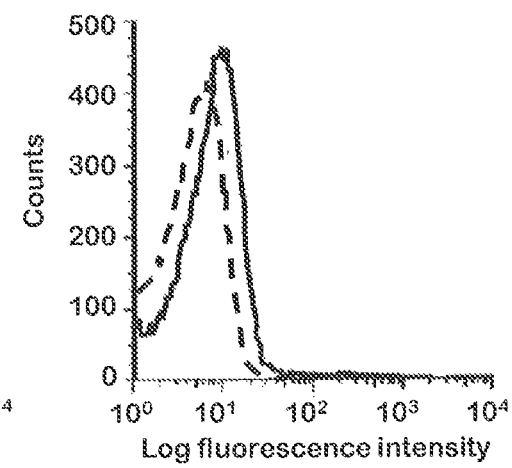
Fig. 1C  Fig. 1D

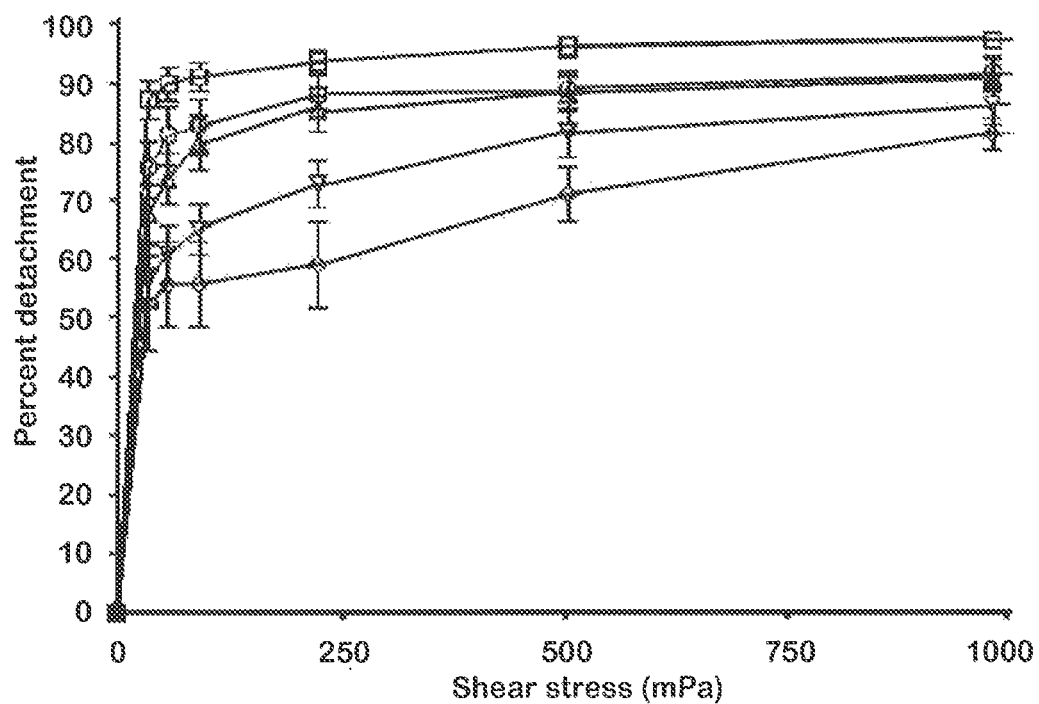
Fig. 4A
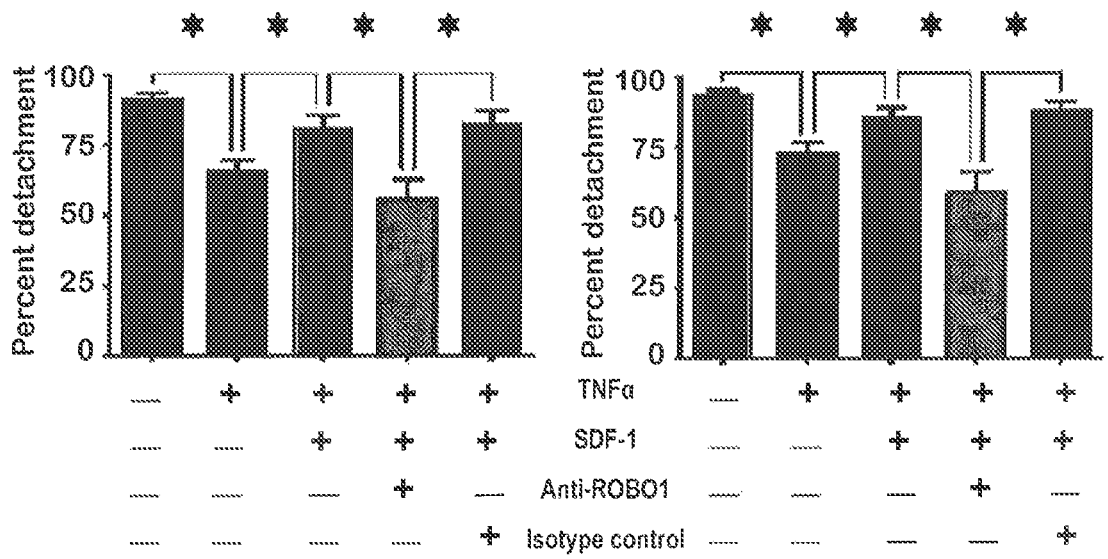
Fig. 4B
Fig. 4C

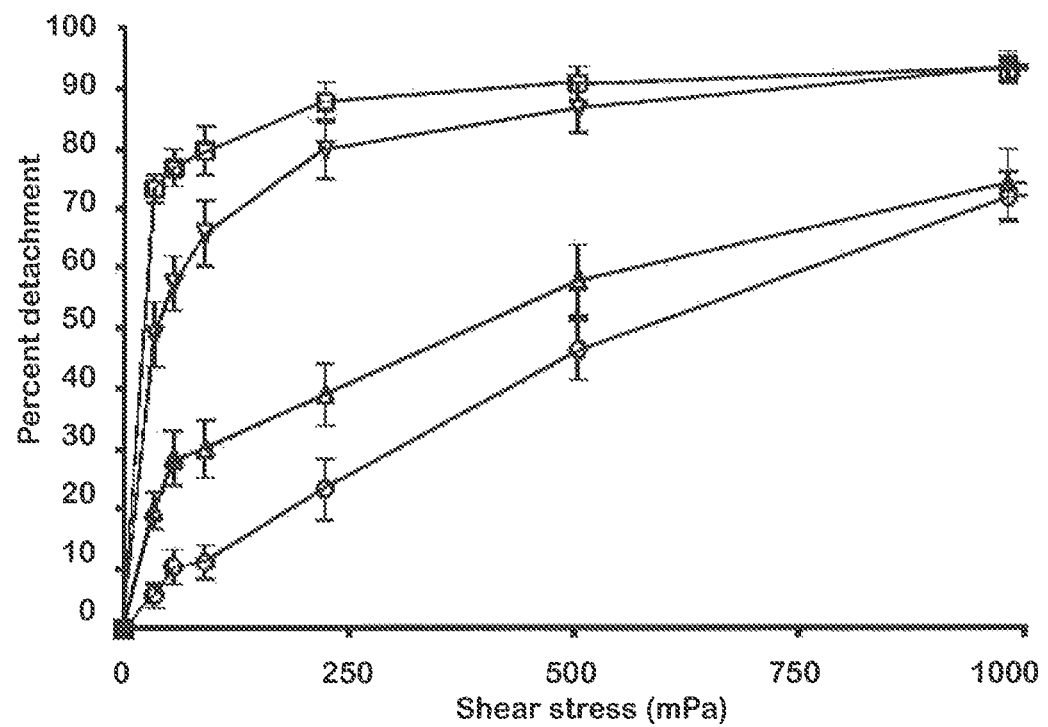
Fig. 5A
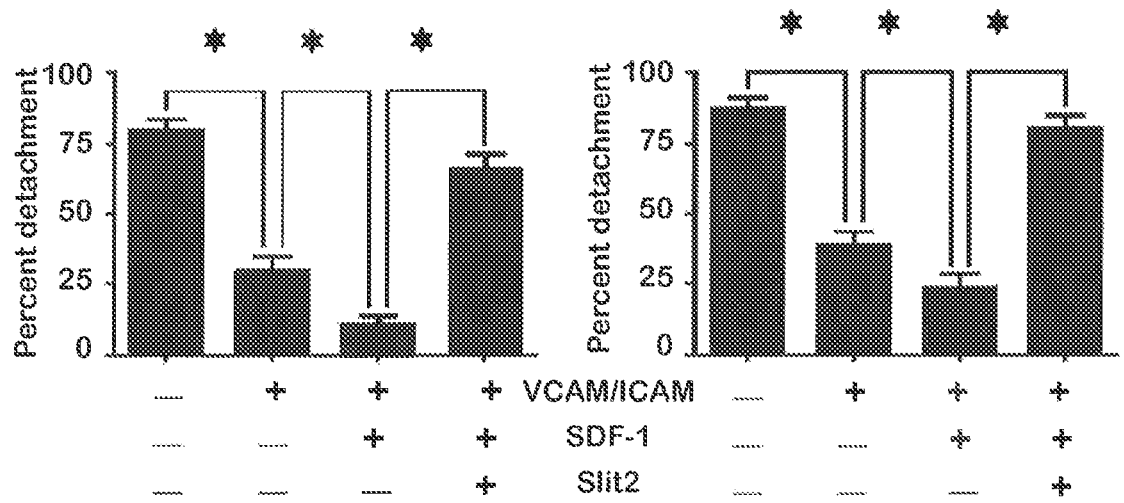
Fig. 5B
Fig. 5C

CXCR4 AND ROBO1 EXPRESSION AS MARKERS FOR AUTOIMMUNE DIABETES

The benefit of the Sep. 13, 2012 filing date of U.S. provisional patent application Ser. No. 61/700,429 is claimed under 35 U.S.C. § 119(e). The complete disclosure of the priority application is hereby incorporated by reference in its entirety.

TECHNICAL FIELD

This invention pertains to biomarkers for type 1 diabetes, and to compounds useful for inhibiting type 1 diabetes.

BACKGROUND ART

Stromal cell-derived factor 1 (SDF-1), also known as C-X-C ligand 12, is a small, 8 kDa chemokine involved in leucocyte activation and chemotaxis. The receptors for SDF-1 are C-X-C receptors CXCR7 and CXCR4, the latter of which only binds SDF-1 and ubiquitin. CXCR7 possesses a tenfold higher affinity for SDF-1 than CXCR4. CXCR7 is expressed at very low levels by T cells. SDF-1 promotes cell adhesion, trans-endothelial migration and chemotaxis. SDF-1 can mediate chemorepulsion responses that may have pathophysiological importance.

Several agonists and antagonists that interact with CXCR4 have been developed. The small peptide agonist CTCE-0214 increases migration of $CD34^+$ cells, although at much higher concentrations than SDF-1, and it may be beneficial in treating systemic inflammation. The peptide antagonist CTCE-9908 increases leukocyte uropod formation, but has no effect on migration or adhesion. E. Aboumrad et al. (2007) The CXCR4/CXCL12 (SDF-1) signalling pathway protects non-obese diabetic mouse from autoimmune diabetes. Clinical and experimental immunology 148: 432-439 reported that disruption of SDF-1-CXCR4 binding by the CXCR4 antagonist AMD3100 can accelerate the development of diabetes in adoptive transfer models in mice, and that it can induce beta cell apoptosis; and suggested that $CXCR4^+$ T cells might be protective against diabetes.

ROBO1, a receptor for SLIT2, has been reported to modulate SDF-1-CXCR4 signaling in tumor cells. See A. Prasad et al., Slit protein-mediated inhibition of CXCR4-induced chemotactic and chemoinvasive signaling pathways in breast cancer cells. J Biol Chem. 2004 Mar. 5; 279(10): 9115-24.

C. Sharp et al. (2008) Stromal cell-derived factor-1/CXCL12 stimulates chemorepulsion of NOD/LtJ T cell adhesion to islet microvascular endothelium. Diabetes 57: 102-112 reported that SDF-1 is involved in recruitment of T cells to the pancreas in type 1 diabetes. The injection of mice with antibodies against SDF-1 altered the development of diabetes and suppression of insulitis. Under shear stress in vitro, SDF-1 promoted adhesion and reduced detachment of C57BL/6J T cells, but decreased adhesion and increased detachment of NOD T cells. T cells from C57BL/6J and NOD/ShiLtJ mice had differing affinities for adhering to SDF-1-treated endothelial cells in vitro. The paper speculated that SDF-1 might mediate chemorepulsion of diabetogenic T cell adhesion to islet microvascular endothelium through unknown mechanisms in NOD mice.

Members of the SLIT protein family (SLIT1, SLIT2 and SLIT3) are large glycoproteins that are important for nervous system development. The SLIT proteins are also expressed by epithelial and endothelial cells. The SLIT molecules bind to members of the roundabout, axon guidance receptor (ROBO) family of receptors. They also interact with heparan sulphate chains. In retinal axons in vivo, SDF-1 modulates SLIT and ROBO signalling, while in leucocytes SLIT2 modulates SDF-1-mediated chemotaxis, trans-endothelial migration and adhesion of T cells, and migration of dendritic cells.

MHC haplotypes and autoantibodies have been suggested as markers for autoimmune (type 1) diabetes, but both are subject to high rates of false positives and false negatives.

There is an unfilled need for improved biomarkers for type 1 diabetes. There is also an unfilled need for therapeutic compounds to reduce the progression of type 1 diabetes, and to reduce the risk of developing type 1 diabetes in patients who are at risk of developing type 1 diabetes.

DISCLOSURE OF THE INVENTION

We have discovered that CXCR4 and ROBO-1 are biomarkers associated with autoimmune (type 1) diabetes. Expression of CXCR4 and ROBO-1 in peripheral CD3 T cells is substantially higher in patients with autoimmune diabetes (type 1 diabetes) than in non-diabetic patients. We have also discovered novel therapies to reduce the progression of type 1 diabetes, and to reduce the risk of developing type 1 diabetes in patients who are at risk of developing type 1 diabetes.

The two receptors CXCR4 and ROBO-1 show increased expression in CD3 T cells both from NOD mice (a mouse model for type 1 diabetes) and from human patients with type 1 autoimmune diabetes, as compared to expression levels in normal mice and non-diabetic humans. It has not previously been reported that SLIT2/ROBO1 plays a role diabetic autoimmune T cell signaling.

We have examined the mechanisms of SDF-1-induced detachment of NOD T cells and the role of SLIT-ROBO interactions. We found that an SDF-1 peptide mimetic can affect the development of adoptive transfer of diabetes in NOD/LtSz $Rag1^{-/-}$ mice.

We measured the levels of CXCR4 and ROBO1 in the T cells of C57BL/6J and NOD/ShiLtJ mice. CXCR4 levels in NOD/ShiLtJ T cells (mouse diabetes 1 model) were significantly greater than those in C57BL/6J T cells (non-diabetic mouse). We found no significant expression of CXCR7 in either C57BL/6J or NOD/ShiLtJ T cells, consistent with our hypothesis that SDF-1-induced adhesion is mediated primarily by CXCR4. We also found that ROBO1 levels were significantly higher in the NOD/ShiLtJ T cells, implying that increased SLIT2 and ROBO1 signalling cause subsequent reversal of the adhesive effects of SDF-1.

Interestingly, we found that CXCR4 and ROBO1 protein expression increased over time in NOD/ShiLtJ CD3 T cells. This increase coincided with the development of hyperglycaemia. This observation, coupled with the fact that CXCR4 and SLIT2-ROBO1 dual engagement mediates chemorepulsion, suggest an adaptive response to limit autoimmune leucocyte recruitment. Insulitis occurs many weeks before the onset of frank hyperglycaemia in NOD/ShiLtJ mice. Surprisingly, steady-state mRNA levels of Cxcr4 and Robo1 did not increase as protein expression increased over time. In fact, Cxcr4 mRNA levels significantly decreased over time. The divergence of changes in protein and mRNA expression shows that post-transcriptional regulation of gene expression is responsible for the observed differences.

We also measured expression of CXCR4 and ROBO1 in human T cells from diabetic and control participants to confirm that increased ROBO1 and CXCR4 expression was not unique to the NOD/ShiLtJ mouse model. We found that CXCR4 expression and ROBO1 expression were both significantly elevated in type 1 diabetic patients versus non-diabetic controls. Interestingly, we also found that the difference between non-diabetic and type 1 diabetic human participants was even more pronounced than that between C57BL/6J and NOD/ShiLtJ mice. Furthermore, while CXCR4 remained elevated in type 1 diabetic patients over one year after initial diagnosis, ROBO1 expression was reduced in long-term type 1 diabetic patients. Thus, CXCR4 and ROBO1 expression profiles serve as unique biomarkers for diagnosis or 'therapeutic windows' for type 1 diabetes.

After demonstrating that NOD/ShiLtJ mice have higher levels of T cell ROBO1 than their C57BL/6J counterparts, we investigated whether the blocking of SLIT2-ROBO1 binding with a blocking antibody against ROBO1 would restore the adhesive effect of SDF-1-CXCR4 binding. Our results clearly demonstrated that SLIT2-ROBO1 binding is involved in SDF-1-mediated detachment in NOD T cells, providing additional evidence that increased ROBO1 in NOD T cells is responsible for this detachment. Next, by replacing endothelial cells with recombinant VCAM-1- and ICAM-1-coated plates, we were able to unequivocally demonstrate that SDF-1 increases NOD/ShiLtJ T cell adhesion in the absence of SLIT2-ROBO1 signalling, and that the addition of SLIT2 mediates SDF-1-dependent chemorepulsion of firm adhesion.

We also found that a stabilized SDF-1 peptide mimetic, CTCE-0214, can reduce NOD/ShiLtJ T cell adhesion to islet endothelial cell monolayers in vitro. We tested the agonist CTCE-0214 in an adoptive transfer model of type 1 diabetes, which progresses much more rapidly than the spontaneous development of diabetes in NOD/ShiLtJ mice. We found that CTCE-0214 significantly delayed the onset of hyperglycaemia. These data clearly demonstrated that modulation of SDF-1 signalling responses for diabetogenic T cell recruitment affected disease development in a mouse model that is destined to develop diabetes. This approach will also be useful in altering T cell recruitment during spontaneous diabetes development in humans.

These biomarkers can be used either alone or in combination with other type 1 diabetes biomarkers to determine autoimmune diabetes incidence or susceptibility. The present invention provides greater clinical ability and accuracy in identifying individuals who are at risk or who have autoimmune diabetes.

In preliminary experiments we have measured C-X-C receptor (CXCR4) and ROBO1 protein expression in both mouse and human T cells. Parallel plate flow chamber adhesion and detachment studies were performed to examine the molecular importance of ROBO1 and SLIT2 for SDF-1-mediated T cell chemorepulsion. Diabetogenic splenocyte transfer was performed in NOD/LtSz Rag1$^{-/-}$ mice to examine the effect of the SDF-1 mimetic CTCE-0214 on adoptive transfer of diabetes.

The data from our preliminary experiments revealed a novel molecular pathway that regulates diabetogenic T cell recruitment and affects the onset of autoimmune diabetes. Our data also showed that SDF-1 may be beneficial or detrimental during the development of diabetes, depending on the levels of T cell ROBO1 and locally expressed SLIT2.

The SDF-1 peptide mimetic CTCE-0214 appeared to be therapeutically beneficial, to alter the progression of autoimmune diabetes, at 10 mg/kg, but to have almost no effect at 1 mg/kg. The dosing frequency appeared to be significant, with a better reduction in the incidence of hyperglycaemia at a dosing of once per week rather than three times per week. Without wishing to be bound by this hypothesis, we propose that the mechanism underlying this surprising result may be that frequent dosing with the SDF-1 agonist CTCE-0214 may stimulate an innate immune response more, versus a specific autoimmune cell response. In other words, a sufficient dose at a longer duration interval may work to selectively affect autoimmune cells versus other immune cells Higher levels of CXCR4, both in human type 1 diabetic patients and in a NOD/ShiLtJ mouse model, appeared to increase SDF-1-CXCR4 signalling, resulting in greater adhesion affinity of T cells for endothelial cells, which in turn increased the recruitment of T cells to the pancreas. Conversely, increased expression of ROBO1 appears to be a complementary regulatory response that reduced the recruitment of overly aggressive T cells, and produced a chemorepulsive effect against SDF-1 that delayed the onset of autoimmune diabetes.

BRIEF DESCRIPTION OF THE DRAWINGS

FIGS. 1a and 1b depict densitometric analyses of the expression of CXCR4 and ROBO1, respectively, in NOD/ShiLtJ (LtJ) mice. FIGS. 1c and 1d depict flow cytometric analyses of extracellular CXCR7 in C57BL/67 and NOD/ShiLtJ mice, respectively.

FIG. 4a depicts detachment of NOD/ShiLtJ T cells from MS1 endothelial cells at different shear stress levels under different treatments: TNFα, SDF-1, or blocking antibody against ROBO1. FIGS. 4b and 4c depict percent detachment of NOD/ShiLtJ T cells under different treatments at 91 mPa and 224 mPa, respectively.

FIG. 5a depicts detachment of NOD/ShiLtJ T cells from VCAM-1- and ICAM-1-coated plates under different treatments: TNFα, SDF-1, or blocking antibody against ROBO1. T, for cells exposed to shear stress in vitro. FIGS. 5b and 5c depict percent detachment of NOD/ShiLtJ T cells under different treatments at 91 mPa and 224 mPa, respectively.

MODES FOR CARRYING OUT THE INVENTION

Figure 2A:
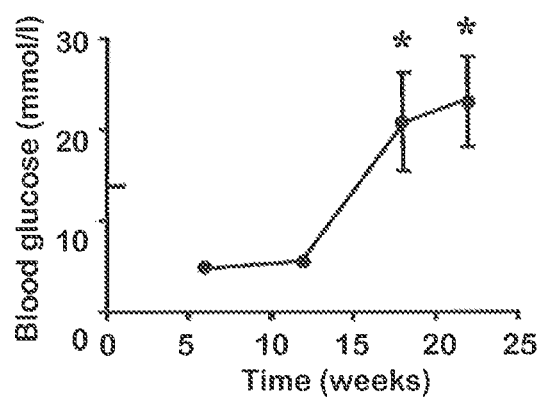
FIG. 2a depicts blood glucose levels for NOD/ShiLtJ mice as a function of time during disease progression.

Embodiments of the invention include the following: 1) assaying CXCR4 or ROBO1 protein expression for mRNA transcription) in T cells as a biomarker for autoimmune diabetes diagnosis or risk (with or without also including traditional clinical indicators of autoimmune diabetes), 2) assaying temporal changes in CXCR4 or ROBO1 protein expression as an indicator of autoimmune diabetes disease progression or therapeutic treatments; and 3) the use of small peptide agonists of SDF-1 as therapeutics for autoimmune diabetes.

Material and Methods

Abbreviations

| | |
|---|---|
| BSA | Bovine serum albumin |
| C57BL/6J | An inbred strain of mice |
| CD3 | A T cell co-receptor |
| CXCR | C-X-C receptor |
| DMEM | Dulbecco's Modified Eagle Medium |
| FBS | Fetal bovine serum |
| FITC | Fluorescein isothiocyanate |
| HBSS | Hanks' balanced salt solution |
| ICAM-1 | Intercellular cell adhesion molecule 1 |
| NOD/LtSz Rag1$^{-/-}$ | Mouse model for diabetes |
| MS1 | Mouse endothelial cells |
| NOD/ShiLtJ | Mouse model for type 1 diabetes |
| PBS | Phosphate-buffered saline |
| ROBO | Roundabout, axon guidance receptor |
| RT-PCR | Reverse transcriptase-polymerase chain reaction |
| SDF-1 | Stromal cell-derived factor 1 |
| SLIT | Slit protein or homologue |
| TBS | TRIS buffered saline |
| TNFα | Tumor necrosis factor alpha |
| VCAM-1 | Vascular cell adhesion molecule 1 |

Example 1. Animals

Mice were housed at the Louisiana State University Health Sciences Center (LSUHSC)-Shreveport Animal Resource Facility, which is accredited by the Association for Assessment and Accreditation of Laboratory Animal Care, and maintained according to the National Research Council Guide for Care and Use of Laboratory Animals. Experiments were conducted in compliance with the Institutional Animal Care and Use Committee. Female NOD/ShiLtJ, NOD/LtSz Rag1$^{-/-}$, and C57BL/6J mice were purchased from the Jackson Laboratory (Bar Harbor, Me., USA). Cohorts of NOD/ShiLtJ mice were killed at 6, 12, 18, and 22 weeks to examine protein and gene expression changes during the progression of autoimmune diabetes.

Example 2. T Cell Isolation

CD3 T cells isolated from splenocytes of female NOD/ShiLtJ or C57BL/6J mice were negatively selected using the EasySep Mouse T Cell Enrichment kit (Stem Cell Technologies, Vancouver, BC, Canada). To obtain human T cells, blood was drawn from either type 1 (n=16) or type 2 (n=5) diabetic patients or from healthy controls (n=11). Participants gave informed consent, following procedures approved by the Institutional Review Board at LSUHSC-Shreveport (Protocol H08-070). T cells were negatively selected from 20 ml blood using a RosetteSep human T cell enrichment cocktail (Stem Cell Technologies).

Example 3. Western Blots

T cells were isolated as described in Example 3 and lysed in radioimmunoprecipitation assay buffer (50 mM TRIS-HCl, pH 8.0, 150 mM NaCl, 1% (vol/vol) Nonidet-40, 0.5% (wt/vol) deoxycholate, and 0.1% (wt/vol) SDS) supplemented with 0.1 µM leupeptin, 0.3 µM aprotinin, and 1 µM phenylmethylsulfonyl fluoride. Whole-cell protein homogenates (12.5 µg total protein) were loaded onto 10% polyacrylamide SDS gels and electrophoresed. Gels were transferred overnight to Immobilon-P7 (Bio-Rad, Hercules, Calif., USA), and subsequently membranes were blocked for 2 hours with 5% (wt/vol BSA) (ROBO1), or with 5% (wt/vol) non-fat dry milk (CXCR4) in TRIS-buffered saline (TBS). Membranes were incubated overnight at 4° C. with antibodies against ROBO1 (vRobo1; Developmental Studies Hybridoma Bank, Iowa City, Iowa, USA) or against CXCR4 (ab2074; Abcam, Cambridge, Mass., USA) at a dilution of 1:100 (0.27 µg/ml) or 1:500, respectively, in blocking buffer supplemented with 0.1% (vol/vol) Tween-20. The remaining washes and incubations were performed at room temperature in TBS containing 0.1% (wt/vol) milk and 0.1% (vol/vol) Tween-20. To validate the specificity of the CXCR4 antibody, additional blots were preincubated either with or without an equal concentration of the CXCR4 peptide (ab8126; Abcam, i.e., the immunogen for the antibody).

For ROBO1 membranes were washed three times for 5 minutes, and then incubated for 2 hours at room temperature with peroxidase-conjugated anti-mouse IgM secondary antibody (A8786; Sigma-Aldrich, St Louis, Mo., USA) at a dilution of either 1:2000 (mouse) or 1:500 (human). For CXCR4, membranes were washed as above and incubated for 2 hours with peroxidase-conjugated anti-rabbit antibody (A0545; Sigma-Aldrich) at 1:2000 dilution. After three 10 minute washes, membranes were rinsed for 10 minutes in TBS. Chemiluminescence was then performed using enhanced chemiluminescence detection reagents (GE Healthcare, Little Chalfont, UK). Various exposures to Hyblot film (E3018; Denville Scientific, South Plainfield, N.J., USA) were performed to ensure exposure linearity. Films were scanned and quantified using Image J (National Institutes of Health, Bethesda, Md., USA), with densitometric values being normalized versus actin expression (as a control), and reported as mean±SEM.

Example 4. Flow Cytometry

Splenocytes were isolated as described in Example 3, Fc-blocked for 15 minutes at room temperature with 5 µg/10$^6$ cells of anti-mouse CD16/CD32 (14-0161-82; eBioscience, San Diego, Calif., USA) and incubated for 20 minutes at room temperature with 0.8 µg/10$^6$ cells of allophycocyanin-conjugated anti-mouse CXCR7 clone 11G8 (FAB4227A; R&D Systems, Minneapolis, Minn., USA) and 0.3 µg/10$^6$ cells of FITC-conjugated anti-mouse CD3 (553062; BD Biosciences, San Jose, Calif., USA). Cells were rinsed twice in PBS containing 2% (vol/vol) FBS, and 10,000 events per sample were collected and analyzed using FacsCalibur (BD Biosciences) and CellQuest software (BD Biosciences).

Example 5. RNA Isolation and Quantitative RT-PCR

Quantitative RT-PCR analysis was performed as otherwise described in K. Fang et al. (2011) Temporal genomewide expression profiling of DSS colitis reveals novel inflammatory and angiogenesis genes similar to ulcerative colitis. Physiological genomics 43: 43-56. Total RNA was isolated using an RNeasy Isolation Kit (Qiagen, Hilden, Germany). Reverse transcription was carried out using 1 µg total RNA from each sample. Primers for Cxcr4 and Robo1 were designed using otherwise standard techniques and the Beacon Designer software package (Premier Biosoft, Palo Alto, Calif., USA). A 40-fold dilution of cDNA was used as a template to perform quantitative RT-PCR with iQ SYBR Green Supermix (Bio-Rad). Gapdh was used as an internal control gene for the PCR reactions. The threshold cycle ($C_t$) formula was used to calculate changes in gene expression.

Example 6. Cell Culture

MS1 mouse pancreatic islet endothelial cells (CRL-2279; ATCC, Manassas, Va., USA) were cultured in DMEM supplemented with L-glutamine, penicillin, streptomycin and 5% (vol/vol) FBS (Atlanta Biologicals, Lawrenceville, Ga., USA). Cultures were maintained in 5% $CO_2$ at 37° C. Cells were grown to confluence in T75 flasks, and seeded in 35 mm tissue culture dishes.

Example 7. In Vitro Hydrodynamic Flow Chamber Adhesion Assays

Hydrodynamic flow chamber assays were performed as otherwise described in C. Sharp et al. (2008). Briefly, T cells isolated as described above were labeled with CellTracker Green (C7025; Life Technologies, Carlsbad, Calif., USA), rinsed, and resuspended at a concentration of $2\times10^6$ cells/ml in phenol red-free Hanks' balanced salt solution (HBSS). The cells were placed in a beaker that had been previously coated with Sigmacote (Sigma-Aldrich), kept at 37° C., and stirred at 60 rev/min. A flow chamber insert and gasket with a 0.5 cm flow width and 250 µm thickness (GlycoTech, Gaithersburg, Md., USA) were used with 35 mm cell culture dishes containing confluent MS1 cell cultures to form a parallel plate flow chamber. To activate endothelial cells, MS1 cells were treated for 4 to 6 hours at 37° C. with 10 ng/ml recombinant mouse TNFα (T7539; Sigma).

For the SDF-1 peptide mimetic T cell adhesion assay, MS1 cells were rinsed with HBSS and treated for 10 minutes with an SDF-1 peptide mimetic (AYWKENKEQ with two branched lysines as a linker between the two motifs, SEQ ID NO 1) at 0.5, 1, 5, or 10 µg/ml. This peptide was a linearized version of a cyclized SDF-1 analogue reported by Tudan et al., "C-terminal cyclization of an SDF-1 small peptide analogue dramatically increases receptor affinity and activation of CXCR4 receptor," J. Med. Chem., vol. 45, pp. 2024-31 (2002). T cells were pumped through polypropylene tubing by a syringe pump (KD Scientific, Holliston, Mass., USA) across the endothelial monolayer at a physiological shear stress of 150 mPa. Real-time digital video images (minimum 28 frames/second) were captured with an epifluorescence microscope (TE-2000 Eclipse; Nikon, Tokyo, Japan) and digital camera (Model C4742-95-12ER: Hamamatsu Photonics, Hamamatsu, Japan). Simple PCI software (Hamamatsu Photonics) was used to analyze the video and to measure T cell rolling velocities. Cells were considered firmly adherent if they remained stationary for 10 seconds within the field of view. A minimum of three videos per plate and four plates per condition were used for analysis.

T cell detachment assays were performed as otherwise described in C. Sharp et al. (2008). T cells were injected into the tubing via an inlet port upstream of the flow chamber at a concentration of $2\times10^6$ cells/ml and allowed to firmly adhere under static conditions for 15 minutes. Next, shear stress was initiated and increased in a step-wise manner every 30 seconds as follows: 35, 56, 91, 224, 504, and 980 mPa. The assay was recorded by video, which was analyzed to determine the percentage of cells detached at the end of each shear stress interval. For the anti-ROBO1 detachment assay, MS1 cells were treated for 10 minutes at 37° C. with TNFα as described above and then with 100 ng/ml recombinant mouse SDF-1α (460-SD; R&D Systems). T cells were pre-treated for 30 minutes at 37° C. with 20 µg/ml ROBO1 blocking antibody (GT15144; Neuromics, Edina, Minn., USA) or isotype control (GT15900; Neuromics).

For the SLIT2 detachment assay, the following modifications were made. Vascular cell adhesion molecule 1 (VCAM-1)- and intercellular cell adhesion molecule 1 (ICAM-1)-coated plates were substituted for confluent monolayers of MS1 cells to isolate the specific ligand and receptor interactions involved. Plates were treated by tracing five 5 mm diameter circles aligned in one row in the center of a 100 mm diameter tissue culture dish using a PAP pen, and then applying 15 µl of 1 mg/ml protein A to each circle for 30 minutes. Plates were rinsed twice with PBS and blocked for 30 minutes with 5% (wt/vol) BSA in PBS. Plates were rinsed and each circle was then treated for 30 minutes with 15 µl of a solution containing 5 µg/ml ICAM-1/Fc chimera (796-IC; R&D Systems) and 5 µg/ml VCAM-1/Fc chimera (643-VM; R&D Systems), or PBS (control). Plates were rinsed and stored at 4° C. T cells were suspended in HBSS containing, 10 µg/ml heparin sodium and treated for 15 minutes at 37° C. with 250 ng/ml SDF-1 and 20 µg/ml recombinant mouse SLIT2 (5444-SL; R&D Systems) before use. A Glycotech rectangular flow chamber with a 250 µm thick gasket and a 1 cm wide flow path was used.

Example 8. Diabetes Adoptive Transfer

Single cell suspensions of splenocytes were isolated from spleens of spontaneously diabetic female NOD/ShiLtJ mice as otherwise described in J. Glawe et al. (2009) Genetic deficiency of Itgb2 or ItgaL prevents autoimmune diabetes through distinctly different mechanisms in NOD/LtJ mice. Diabetes 58: 1292-1301, Erythrocytes were lysed with 150 mM $NH_4Cl$, 1.0 mM/l $KHCO_3$, and 0.1 mM disodium EDTA, and then resuspended in PBS at $200\times10^6$ splenocytes per ml. Female NOD/LtSz Rag1$^{-/-}$ mice were injected retro-orbitally with $20\times10^6$ splenocytes.

The recipient mice were then injected retro-orbitally, either once or three times per week, with the SDF-1 peptide mimetic CTCE-0214 (SEQ ID NO. 2, KPVSLSYRCP-CRFF-Linker-LKWIQEYLEKALN-OH) (British Canadian BioSciences, Vancouver, BC, Canada) at 1 or 10 mg/kg, or with PBS. See K Li, et al., "Small peptide analogue of SDF-1a supports survival of cord blood CD34+ cells in synergy with other cytokines and enhances their ex vivo expansion and engraftment into nonobese diabetic/severe combined immunodeficient mice," Stem Cells, vol, 24, pp. 56-64 (2006); R. Zhong et al., "Small peptide analogs to stromal derived factor 1 enhance chemotactic migration of human and mouse hematopoietic cells," Experimental Hematology, vol 32, pp. 470-475 (2004); A. Faber at al., "The many facets of SDF-1, CXCR4 agonists and antagonists on hematopoietic progenitor cells," *Journal of Biomedicine and Biotechnology*, Article ID 26065; doi: 10.1155/200726065 (2007). Blood glucose was measured twice per week via a tail stick assay (Ascensia Glucometer Elite; Bayer, Leverkusen, Germany). Mice were considered hyperglycaemic following two consecutive measurements at 13.9 mM (250 mg/dl) glucose. Another SDF-1 mimetic that could be used is the CTCE-9908 peptide disclosed by A. Faber at al. (2007).

Results

Example 9. Results

Summary of experimental results: CXCR4 and ROBO1 protein expression increased in diabetic NOD/ShiLtJ T cells over time, and coincided with the onset of hyperglycaemia. CXCR4 and ROBO1 expression was also elevated in human type 1 diabetic T cells, with ROBO1 expression maximal at less than 1 year post diagnosis. Cell detachment studies revealed that immunoneutralization of ROBO1 prevented SDF-1-mediated chemorepulsion of NOD T cell firm adhesion to TNFα-stimulated islet endothelial cells. SDF-1 increased NOD T cell adhesion to recombinant adhesion molecules, a phenomenon that was reversed by recombinant SLIT2. Finally, we found that an SDF-1 peptide mimetic prevented NOD T cell adhesion in vitro and significantly delayed adoptive transfer of autoimmune diabetes in vivo.

Example 10. CXCR4, ROBO1 and CXCR7 Expression

We first compared expression levels of CXCR4, the receptor for SDF-1, in T cells from C57BL/6J and diabetes-prone NOD/ShiLtJ mice at 12 weeks of age. T cells from NOD/ShiLtJ mice showed increased CXCR4 expression compared with those from C57BL/6J mice (FIG. 1a). We then examined T cell expression levels of ROBO1, a receptor for SLIT2 that is known to modulate the signalling effects of SDF-1 and CXCR4. T cells from NOD/ShiLtJ mice showed significantly higher expression of ROBO1 as compared to those from C57BL/6J mice (FIG. 1b). These data suggested that the different effects of SDF-1 on C57BL/6J and NOD/ShiLtJ mice resulted from different levels of T cell expression of CXCR4 and ROBO1. To determine whether CXCR7 played a role in these observations, we dual-stained splenocytes from NOD/ShiLtJ and C57BL/6J mice with anti-mouse CD3 and anti-mouse CXCR7, and analyzed them by flow cytometry. Staining for CXCR7 in CD3+ cells was minimal in both strains of mice.

Densitometric analysis, with representative western blots, found increased expression of CXCR4 (FIG. 1a) and ROBO1 (FIG. 1b) in T cells from 12-week-old NOD/ShiLtJ (LtJ) mice as compared to those from C57BL/6J mice (*p<0.05). Flow cytometric analysis of T cells from C57BL/67 (FIG. 1c) and NOD/ShiLtJ (FIG. 1d) mice showed only low-level staining for extracellular CXCR7 (solid line). Isotype controls are depicted with a dashed line.

Figure 2B:
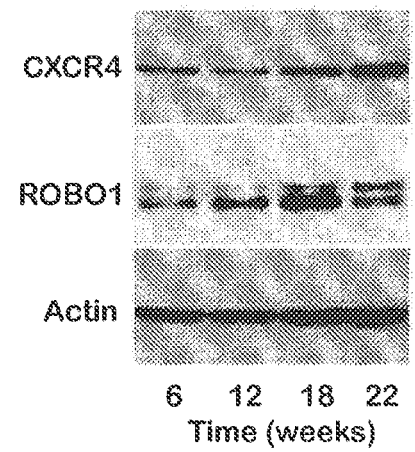
FIG. 2b depicts Western blots of T cell lysates for CXCR4 and ROBO1 at various times for NOD/ShiLtJ mice, with actin as a control.

Having determined that NOD/ShiLtJ CD3 T cells had increased CXCR4 and ROBO1, we observed protein and mRNA levels during the time course of disease progression. FIG. 2a shows that NOD/ShiLtJ mice had significantly increased blood glucose levels by 18 weeks of age. The dashed line at 13.9 mM glucose (250 mg/dl) denotes the threshold for hyperglycaemia. Western blots of T cell lysates for CXCR4 and ROBO1 (FIG. 2b) were quantified by densitometric analysis.

Figure 2C:
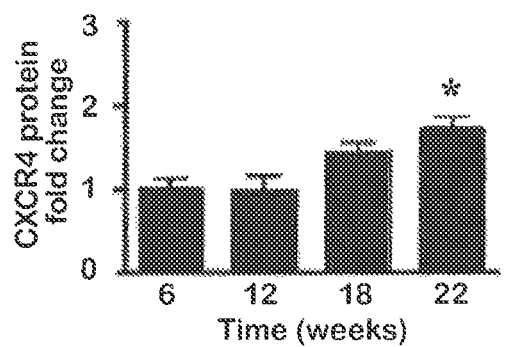
FIGS. 2c and 2d depict CXCR4 and ROBO1 protein levels, respectively, at various times for NOD/ShiLtJ mice.
Figure 2D:
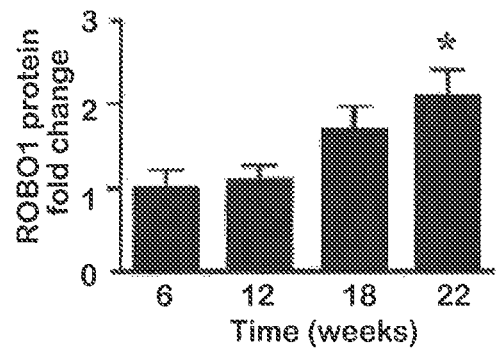
Figure 2E:
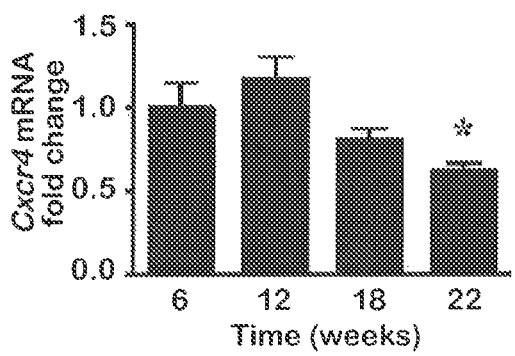
FIGS. 2e and 2f depict Cxcr4 and Robo1 mRNA levels, respectively, at various times for NOD/ShiLtJ mice.
Figure 2F:
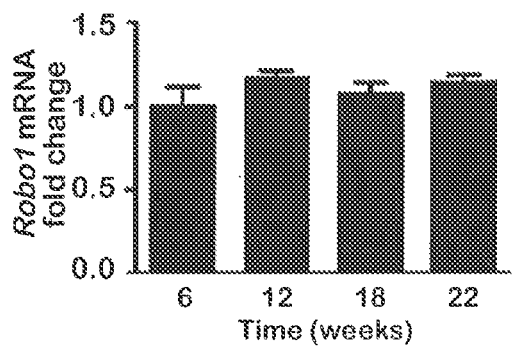

Protein levels of CXCR4 and ROBO1 progressively increased between 12 and 22 weeks of age. NOD/ShiLtJ T cells had significantly increased levels of CXCR4 protein (FIG. 2c) and ROBO1 protein (FIG. 2d) at 22 weeks of age, as compared to either 6 weeks or 12 weeks. Interestingly, FIG. 2e shows that Cxcr4 mRNA levels in T cells significantly decreased over time during diabetes progression (22 weeks of age compared with 12 weeks of age), while FIG. 2f shows that Robo1 mRNA levels in T cells remained essentially unchanged, *p<0.05.

Example 11. Human Type 1 Diabetic Patients have Increased T Cell CXCR4 and ROBO1 Expression Next, we investigated whether similar increases in T cell CXCR4 and ROBO1 expression were seen in human type 1 diabetic patients. CD3 T cells were purified from blood drawn from human type 1 diabetic patients and non-diabetic controls, and CXCR4 and ROBO1 expression were determined by western blot of protein lysates. CXCR4 levels in T cells from type 1 diabetic patients was approximately three times that of non-diabetic controls. There was no statistical difference between recently diagnosed type 1 diabetic patients eel year) and those diagnosed at least 1 year previously. A similar increase was also seen for ROBO1 expression in T cells from type 1 diabetic patients compared with those from healthy controls. Interestingly, a significant increase in ROBO1 expression occurred in type 1 diabetic participants less than 1 year after diagnosis, which subsequently diminished over time. CXCR4 and ROBO1 levels were not elevated in patients recently diagnosed with type 2 diabetes (≤1 year) as compared with non-diabetic controls.

Figure 3A:
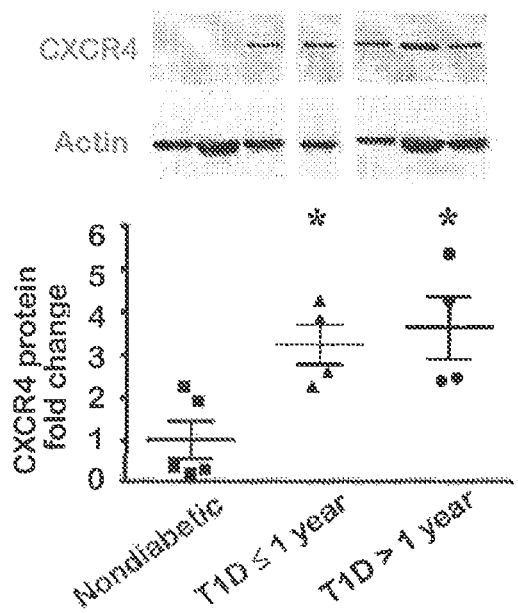
FIGS. 3a and 3b depict western blots and densitometric analyses for expression of CXCR4 protein and ROBO1 protein, respectively, in type 1 diabetic patients.
Figure 3B:
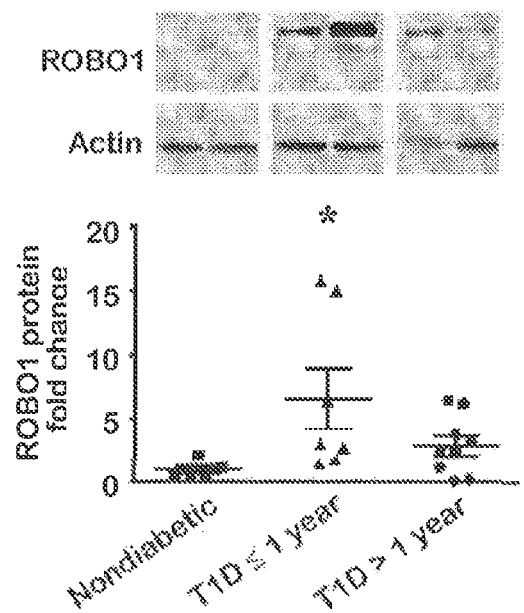
Figure 3C:
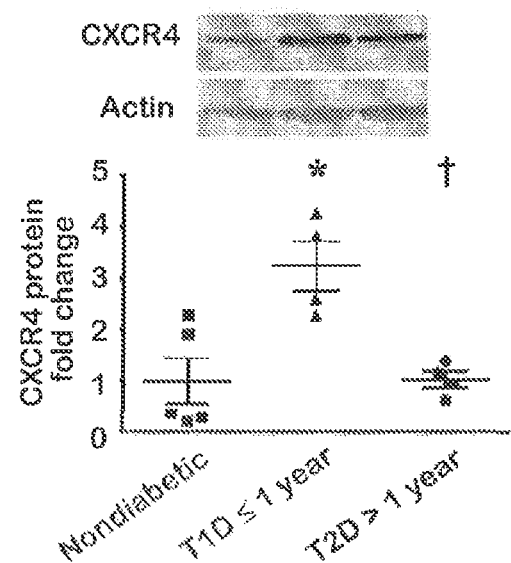
FIGS. 3c and 3d depict western blots and densitometric analyses for expression of CXCR4 protein and ROBO1 protein, respectively, in type 2 diabetic patients.
Figure 3D:
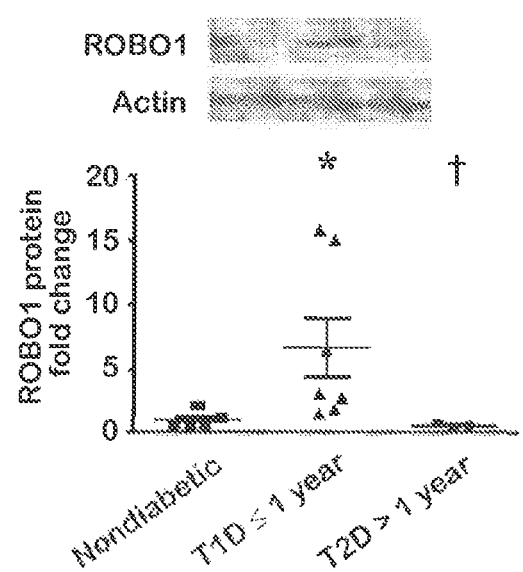

FIG. 3a depicts a densitometric analysis of representative western blots, showing increased expression of CXCR4 in type 1 diabetic patients with ≤1 year and >1 year disease duration, as compared with non-diabetic controls; n=4 for each diabetes group, n=5 for control group; *p<0.05. FIG. 3b depicts analyses and western blots showing increased expression of ROBO1 in recently diagnosed type 1 diabetic patients (n=7) compared with non-diabetic controls, n=5; *p<0.05. No statistically significant difference was seen between either of the above groups and type 1 diabetic patients more than 1 year after diagnosis (n=9). FIG. 3c depicts analyses and western blots showing no increase in CXCR4 in recently diagnosed type 2 diabetic patients (n=4), and a significant difference in CXCR4 levels between recently diagnosed type 1 diabetic patients (n=4), and both non-diabetic (n=5; *p<0.05) and recently diagnosed type 2 diabetic patients (†p<0.05). FIG. 3d depicts no increase in ROBO1 in recently diagnosed type 2 diabetic patients (n=3), but significant differences it ROBO1 levels between recently diagnosed type 1 diabetic patients (n=7) and both non-diabetic (n=5; *p<0.05) and recently diagnosed type 2 diabetic patients (†p<0.05). Table 1 reports patient gender distribution, age, duration of disease, percent $HbA_{1c}$, and autoantibody positivity.

TABLE 1

| Data for diabetic patients | | |
|---|---|---|
| Variable | Type 1 | Type 2 |
| Participants (n) | 15 | 5 |
| Gender-male (n) | 8 | 1 |
| Gender-female (n) | 7 | 4 |
| Mean age (years) | 10.9 (4-17) | 15.7 (14-18) |
| Diabetes duration (years) | 1.8 (0-9) | 3.5 (1-5) |

TABLE 1-continued

Data for diabetic patients

| Variable | Type 1 | Type 2 |
|---|---|---|
| HbA$_{1c}$ (%) | 10.9 (6.7-16.0) | 6.3 (5.1-7.4) |
| HbA$_{1c}$ (mmol/mol) | 95.6 (49.7-151) | 45.3 (32.2-57.4) |
| Autoantibody positivity, % (n) | | |
| GAD-positive | 73.3 (11) | 20 (1) |
| ICA-positive[a] | 20 (3) | 0 (0) |
| IAA-positive[b] | 26.7 (4) | 0 (0) |
| 1 autoantibody | 33.3 (5) | 20 (1) |
| 2 autoantibodies | 33.3 (5) | 0 (0) |
| 3 autoantibodies | 6.6 (1) | 0 (0) |

Unless indicated otherwise, values are mean (range)
[a]ICA, islet cell antibodies; [b]IAA, insulin autoantibodies

Example 12. Anti-ROBO1 Reverses SDF-1-Induced Detachment of NOD T Cells In Vitro Having established that T cell levels of ROBO1 differ between C57BL/6J and NOD/ShiLtJ mice, we investigated whether SDF-1-mediated firm adhesion defects were dependent on ROBO1-SLIT2 binding. We used a parallel plate flow chamber detachment assay. NOD/ShiLtJ T cells were first allowed to statically adhere to islet endothelial cell monolayers. Adherent T cells were then exposed to incrementally increasing shear stress to test whether blocking of ROBO1-SLIT2 binding with an anti-ROBO1 antibody would alter T cell adhesion. TNFα stimulation increased attachment, as expected, compared with control. Adding SDF-1 (TNFα+SDF) reduced adhesion. However, adding an anti-ROBO1 pretreatment (TNFα+SDF+anti-ROBO1) increased adhesion, showing that ROBO1 is involved in mediating the detachment of NOD T cells from SDF-1-treated endothelial cells. The detachment of T cells treated with an isotype control (TNFα+SDF+isotype control) was not significantly different from that of TNFα+SDF-1-treated endothelial monolayers.

FIG. 4a shows that NOD/ShiLtJ T cells did not adhere to unstimulated MS1 endothelium (squares) in vitro. TNFα stimulation of MS1 cells (downward-pointing triangles) increased the resistance of T cells to shear-mediated detachment. Incubation of MS1 cells with SDF-1 reduced the adhesion of T cells to TNFα-activated endothelium (upward-pointing triangles). Incubation of T cells with a blocking antibody against ROBO1 blocked SDF-1-induced detachment from TNFα-activated endothelium (diamonds). Percent detachment is shown at 91 mPa (FIG. 4b) and 224 mPa (FIG. 4c); *p<0.05

Example 13. SLIT2 Reverses the Effect of SDF-1 on T Cell Adhesion

To confirm the significance of ROBO1-SLIT2 binding, we next examined the effect of SLIT2 on T cell adhesion. Because SLIT2 is expressed in endothelial cells, plates coated with recombinant ICAM-1 and VCAM-1 were used in a detachment assay with T cells treated with recombinant SLIT2 protein. ICAM-1- and VCAM-1-coated plates dramatically reduced T cell detachment as compared with BSA controls. T cells pretreated with SDF-1 alone showed increased resistance to shear-mediated detachment as compared with untreated T cells. However, cells treated with both SDF-1 and SLIT2 showed a significant increase in detachment as compared with cells treated with SDF-1 alone, demonstrating that SLIT2-ROBO1 binding regulates SDF-1-mediated chemorepulsion.

FIG. 5a shows that VCAM-1- and ICAM-1-coated plates (upward-pointing triangles) reduced the detachment of NOD/ShiLtJ T cells exposed to shear conditions in vitro as compared with BSA-coated controls (squares). T cells pretreated with SDF-1 exhibited reduced shear-mediated detachment from VCAM-1- and ICAM-1-coated plates (circles) as compared with untreated T cells on the same plates (upward-pointing triangles), whereas the addition of SLIT2 to SDF-1-treated T cells promoted detachment from VCAM-1- and ICAM-1-coated plates (downward-pointing triangles). The percent detachment is shown at 91 mPa (FIG. 5b) and 224 mPa (FIG. 5c); *p<0.05.

Example 14. SDF-1 Peptide Mimetic In Vitro and In Vivo

Figure 6A:
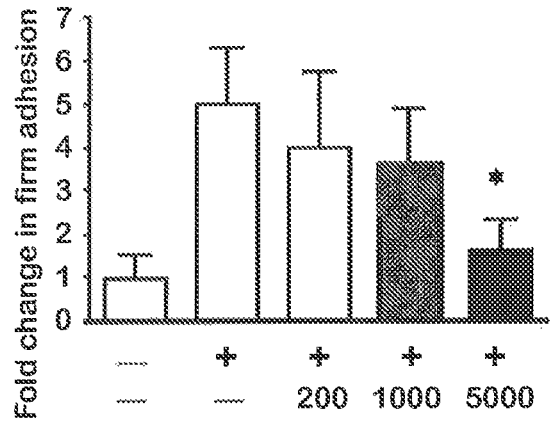
FIG. 6a depicts the effects of different treatments of linear SDF-1 peptide agonist on the adhesion of NOD/ShiLtJ CD3 T cells to TNF-stimulated islet microvascular endothelial cells in response to shear stress in vitro.
Figure 6B:
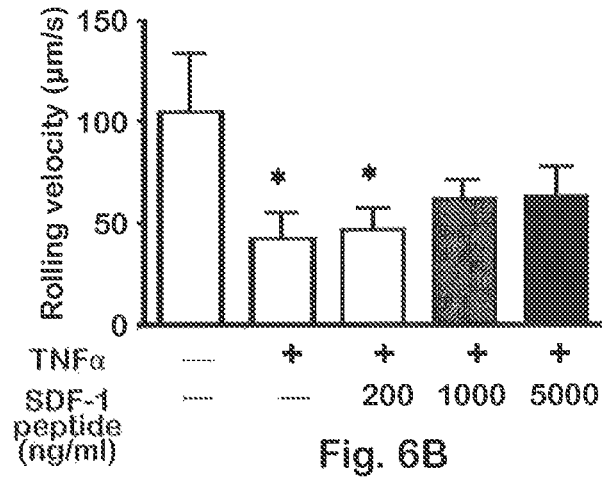
FIG. 6b depicts the effects of different treatments on rolling velocity of treated endothelial cells.

We examined whether a linear SDF-1 peptide mimetic containing the receptor-binding site could replicate the effect of full length SDF-1 in blocking adhesion of T cells to activated endothelium. MS1 cells were treated for 4 hours with 10 ng/ml TNFα, followed by treatment for 10 minutes with an SDF-1 peptide mimetic at 200, 1000, or 5000 ng/ml. Cells were then tested in a parallel plate flow chamber cell adhesion assay. Fluorescently labeled T cells obtained from NOD/ShiLtJ mice flowed over the endothelial monolayers at 150 mPa. FIG. 6a shows that TNFα-induced adhesion was five times greater than that for untreated endothelium, and that this increase was significantly reduced by the SDF-1 peptide mimetic in a dose-dependent manner up to 5 µg/ml. Leucocyte adhesion videos were analyzed to calculate T cell rolling velocity and to determine whether the decrease in firm adhesion was due to a decreased number of rolling cells. The SDF-1 peptide mimetic did not decrease the number of rolling cells (data not shown), nor did it affect the rolling velocity (FIG. 6b).

After showing the effectiveness of the SDF-1 peptide mimetic, we used diabetogenic splenocytes in NOD/LtSz Rag1$^{-/-}$ mice to determine whether a CTCE-0214-stabilised, cyclic SDF-1 peptide that was designed for in vivo use altered the adoptive transfer of diabetes. FIGS. 6c, 6d, 6e, 6f show the effects of different doses of the SDF-1 mimetic peptide in delaying the onset of hyperglycaemia. At a dose of 10 mg/kg, the SDF-1 peptide mimetic effectively delayed adoptive transfer of diabetes, with a more beneficial effect at once-a-week dosing versus three-times-a-week dosing. Together, these data confirmed the role of SDF-1-mediated chemorepulsion responses in regulating the development of autoimmune diabetes.

Figure 6C:
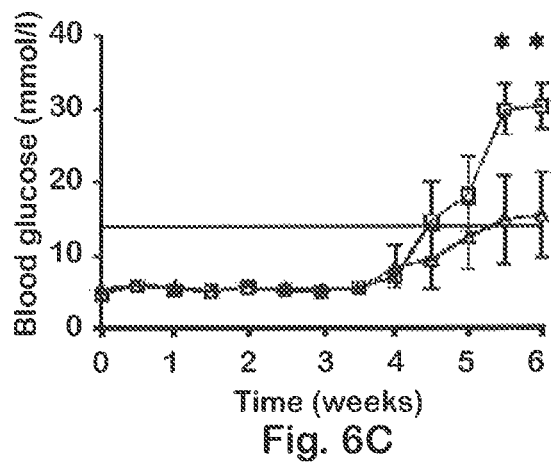
FIG. 6c depicts the effect of the peptide mimetic CTCE-0214 on blood glucose levels during the time course of development of diabetes in a NOD/LtSz Rag1$^{-/-}$ adoptive transfer model in mice.
Figure 6D:
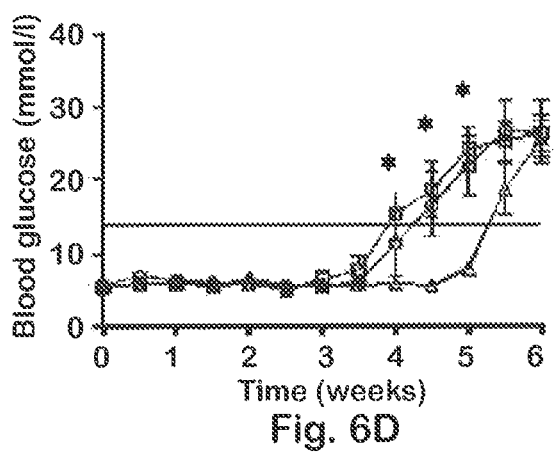
FIG. 6d depicts the effect of the peptide mimetic CTCE-0214 on blood glucose levels during the time course of the development of diabetes in a NOD/LtSz Rag1$^{-/-}$ adoptive transfer model in mice, when the peptide mimetic was administered once per week versus three times per week.
Figure 6E:
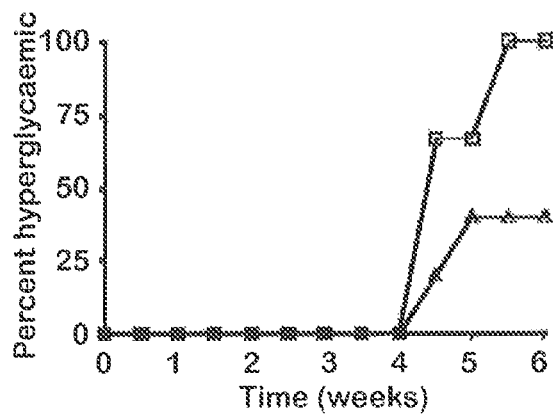
FIGS. 6e and 6f depict the effect of the peptide mimetic CTCE-0214 on hyperglycaemia for treatments once per week versus three times per week, respectively.
Figure 6F:
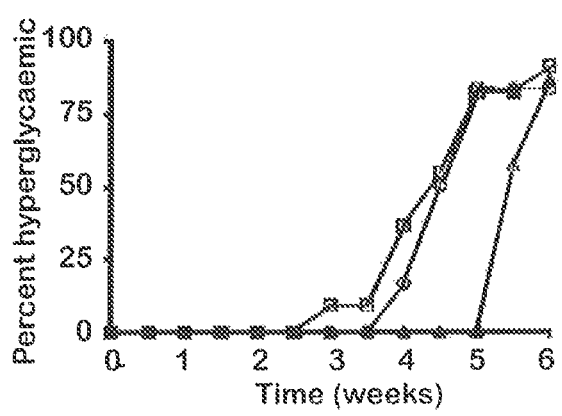

FIG. 6a shows that the SDF-1 peptide mimetic reversed TNFα-mediated adhesion in response to shear stress in vitro in a dose-dependent manner as measured by the fold change in the number Of adherent cells captured by video, versus TNFα alone. FIG. 6b shows that the SDF-1 peptide mimetic did not significantly affect rolling velocity in TNFα-treated endothelial cells, versus the control. FIG. 6c shows that CTCE-0214 slowed the development of diabetes in a NOD/LtSz Rag1$^{-/-}$ adoptive transfer model. At 5.5 and 6 weeks post-transfer, mice treated with 10 mg/kg CTCE-0214 once per week (upward-pointing triangles) showed significantly reduced glucose levels as compared with PBS-treated mice (squares). The dashed line at 13.9 mM glucose denotes the threshold for hyperglycaemia. FIG. 6d shows that at 4 to 5 weeks post-transfer, mice treated with 10 mg/kg (upward-pointing triangles), but not those treated with 1 mg/kg (circles) CTCE-0214 three times per week, showed significantly reduced glucose levels as compared with PBS treatment (squares). Mice treated with CTCE-0214 at 10 mg/kg (upward-pointing triangles) both one (FIG. 6e) and three (FIG. 6f) times per week showed delayed development of hyperglycaemia as compared with PBS treatment (squares).

Example 15. Robo-1 and CXCR4 Expression in CD4 and CD8 T Cells

Robo-1 expression in diabetogenic T cells serves as both a biomarker of diabetes progression and as a negative regulator of diabetogenic T cell recruitment and infiltration. We hypothesize that the Robo-1/Slit-2 receptor-ligand complex negatively regulates pathogenic immune cell recruitment and acts as an endogenous defense against autoimmune cell infiltration. We will demonstrate the use of Slit-2 peptide agonists to prevent or inhibit the development of autoimmune diabetes. As described above, we have shown that CD3 T cell expression of Robo-1 and CXCR4 is increased as compared to healthy or type 2 diabetic patients. We will conduct further studies to determine the expression of Robo-1 and CXCR4 (protein and mRNA) in CD4 and CD8 T cells upon initial diagnosis of autoimmune diabetes, and over time (6 and 12 months post diagnosis).

We will examine Robo-1 and CXCR4 protein and mRNA expression using flow cytometry and qRT-PCR analysis, in a modification of the procedure described above for CD3 T cells. Briefly, T cell CD4 and CD8 fractions will be isolated using negative selection kits from Stem Cell Technologies. T cells will be fixed with 1% paraformaldehyde, permeabilized with 0.05% Triton-X 100 for 5 min, stained with mouse anti-human Robo-1 for 45 min, followed by PE-conjugated anti-human CXCR4(CD184) (clone 12G5, BD Pharmingen) and APC anti-mouse secondary antibodies. Signals will be normalized versus appropriate isotype and negative controls. mRNA will also be isolated from an aliquot of isolated CD4 and CD8 T cells and used to measure Robo1 and Cxcr4 mRNA expression via qRT-PCR. Ther Robo1 and Cxcr4 mRNA levels will be normalized versus Gapdh and beta actin mRNA. Power calculations using data from our earlier experiments indicate that about 30 subjects will be needed to achieve a power of 0.8 to determine statistical differences at the 0.05 level or below. Thus we plan to enroll 40 newly diagnosed type 1 diabetes patients in the study (to account for possible dropouts). A cohort of 30 control age matched subjects (with or without type 2 diabetes) will be enrolled who do not have any known immune disorder, to compare expression profiles between patient cohorts. Expression data will be compared using two way ANOVA between T cell types and patient cohorts.

T cells will be collected from enrolled type 1 diabetes patients at 6 and 12 months following initial diagnosis, and processed as discussed above. Longitudinal Rubra-1 and CXCR4 protein and mRNA expression will be compared to levels upon initial diagnosis using two way ANOVA for changes in expression over time in CD4 and CD8 T cells.

We will determine the relationship between Robo-1 and CXCR4 expression, HLA-DR3 and DR4, and autoantibody positivity. T cell HLA DR3 and DR4 haplotype will be determined. Autoantibody positivity for IAA, GAD65 and ICA will also be determined.

Results from these experiments will demonstrate whether Robo-1 and CXCR4 protein and mRNA in CD4 and CD8 cells can be used for diagnosis of and as biomarkers of disease progression in autoimmune diabetes in a manner similar to what we have demonstrated for CD3 T cells.

Example 16. Robo1/CXCR4 Co-Stimulation in Human Diabetogenic T Cell Chemorepulsion We will examine chemorepulsion mechanisms of human diabetic T cells and the role of Robo-1/CXCR4. We will measure the effect of SDF-1 peptide agonists on human diabetic T cell adhesion under hydrodynamic flow conditions. These in vitro studies will use microfluidic chips patterned after human microvascular networks that emulate biophysical conditions in vivo (commercially available from Syn-Vivo Inc.)

In vitro adhesion studies using the microfluidic chips will be performed using T cells isolated from enrolled patients as outlined in the previous Example. An advantage of the microchip approach is that fewer cells (~1 million) are needed to perform the microfluidic adhesion assays on a simulated microvasculature chip as compared to a traditional parallel plate flow chamber assay. Also, measurements can be taken under a range of different flow conditions. A single 10 ml blood draw from recruited or control subjects will provide sufficient CD4 and CD8 T cells to perform chemorepulsion adhesion assays and molecular phenotyping.

To measure SDF-1 mediated chemorepulsion of human CD4 or CD8 diabetic T cells, we will coat the microfluidic chamber with recombinant endothelial cell adhesion molecules, namely the chimeric proteins ICAM-1/Fc and VCAM-1/Fc. Chambers will also be coated with or without SDF-1 protein to compare the effects of SDF-1 alone on T cell adhesion under flow. Hydrodynamic flow conditions will be controlled using a digital microsyringe pump, to expose adherent T cells to a progressive range of shear stresses (0.25-20 dynes/cm$^2$) over 30 second intervals. T cell detachment responses will be imaged both in 'straight line' portions, and in bifurcated/bent portions of the microfluidic chip vascular network. We will use an automated Nikon TE2000 epifluorescence scope with a digital programmable Ludi X,Y-Z stage to sequentially image a minimum of 8 distinct fields of view over 30 second intervals; n=4 for each flow condition per shear time interval. Each of the same eight distinct fields will be imaged over the course of experiment. Detachment rates will be calculated as described above, and statistically compared using two way ANOVA between SDF-1 versus shear rate.

Example 17. Identifying Slit-2 LRR Domain 2 (D2) Amino Acid Sequences that Modulate SDF-1/CXCR4 Chemorepulsion Our experimental data have shown that the Slit-2 peptide containing the LRR domain 2 stimulated detachment of NOD/LtJ T cells from recombinant endothelial cell adhesion molecules in conjunction with SDF-1. We will confirm that the Slit-2 peptide has similar effects on human diabetic T cell chemorepulsion; and identify the domains associated with this activity. A separate series of T cell detachment assays using microfluidic chambers will be performed using intact Slit-2 LRR Domain 2 peptide (amino acids 268-483, SEQ ID NO. 3) or portions from the LRR Domain 2 parent peptide, designated LRR 1 through LRR 20 (SEQ ID NO. 4-23) or LRR 1 core through LRR 20 core (SEQ ID NO. 24-43). T cell detachment using these various Slit-2 peptides (20 μg/ml) will be measured and calculated as described

Example 18. Confirming the Role of Robo-1 in Slit-2-Mediated Diabetic T Cell Chemorepulsion A series of microfluidic chamber studies will be carried out using chambers coated with recombinant adhesion molecules and SDF-1 agonist. The effect of the combination of a Slit-2 agonist peptide with Robo-1 neutralizing antibody will show that Slit-2 engagement of Robo-1 is necessary for SDF-1 mediated chemorepulsion. 20 µg/ml Robo-1 blocking antibody or isotype control antibody (GT15144 and GT15900 respectively, from Neuromics) will be added with Slit-2 agonist peptides to stimulate shear-dependent chemorepulsion. T cell detachment will be measured and calculated as described above, and statistically compared using two way ANOVA between Robo-1 antibody versus Slit-2 agonist treatments.

We expect that Slit-2 agonist peptide will stimulate human diabetic CD4 and CD8 T cell detachment from recombinant endothelial cell adhesion molecules (ICAM-1 & VCAM-1) in an SDF-1 and shear dependent manner. We will identify the peptide domains primarily responsible for this activity. The invention encompasses the use of one or more of the peptide domains described above for therapy and prevention of autoimmune diabetes.

Example 19. Slit-2 Peptide Agonists Alter the Development of Autoimmune Diabetes This series of experiments will determine (a) the effect of different Slit-2 agonist peptides (e.g., (SEQ ID NO. 4-23) to protect against adoptive transfer diabetes in NOD/Rag-1 mice and (b) the effect of different Slit-2 agonist peptides to prevent spontaneous development of autoimmune diabetes in NOD mice. The agonist peptides that are successful in these experiments in mice should also prove useful for therapy or prevention of autoimmune diabetes in humans.

We will perform adoptive transfer experiments to determine the effect of Slit-2 peptide and peptide agonists at 10 mg/kg and 25 mg/kg doses on diabetogenic T cell recruitment into NOD/Rag-1 pancreatic islets at weeks 1, 2, 3, 4, 5, and 6 weeks by immunohistochemistry for CD3, CD4, and CD8 staining of formalin fixed tissue sections. A control-scrambled peptide will be administered to a separate cohort of reconstituted NOD/Rag-1 mice. Tissue sections will be stained with H&E to look for signs of insulitis.

Splenic and pancreatic lymph node CD3, CD4, and CD8 populations will be analyzed by flow cytometry for each animal at each time point to obtain a clear understanding of diabetogenic lymphocyte distribution patterns. Eight reconstituted NOD/Rag-1 deficient mice will be examined per time point for both the Slit-2 agonist peptide and the scrambled control peptide. Changes in splenocyte T cell linage distribution will be compared by one way ANOVA with Bonferroni post-testing between all time intervals for each of the CD markers. Insulitis will be scored from at least 20 islets per animal using a scoring system 0-4 (0=no insulitis, 1=0-25% insulitis, 2=26-50% insulitis, 3=51-75% insulitis, 4=76-100% insulitis (i.e., complete destruction)). Insulitis scores will be compared by one-way ANOVA with Bonferroni post-testing between all time intervals.

Another set of experiments will be performed to confirm that the Slit-2 LRR D2 peptide agonists can prevent (or inhibit) the spontaneous development of diabetes in NOD mice. 20 female NOD mice will be used for each dosing protocol. Each dosing protocol will be the administration of either Slit-2 agonist or scrambled control peptide, at 25 mg/kg, 10 mg/kg, or 1 mg/kg, twice per week, retro-orbital injection, beginning at week 6 and continuing until the mice become diabetic or 32 weeks, whichever is first. Five mice will be randomly chosen from each peptide dose group at 12 weeks and sacrificed for evaluation of insulitis and specific T cell infiltrates as otherwise described above. After animals are diagnosed as diabetic (two consecutive blood glucose measurements ≥250 mg/dL), they will be euthanized, and the pancreas tissue will be harvested to determine degree of insulitis. Flow cytometry analysis for Robo-1 and CXCR4 expression will be performed with splenic T cell populations from the cohorts sacrificed at 12 weeks, and also upon diagnosis of frank diabetes. Insulitis and T cell FACS population analysis will be statistically compared using one-way ANOVA with Bonferroni post-testing among treatment groups.

We expect that Slit-2 peptide agonist therapy will significantly attenuate the development of insulitis in both the adoptive transfer mouse model and spontaneous mouse model of autoimmune diabetes. Moreover, it is possible that Slit-2 agonist therapy may result in greater splenic retention of CD4 and CD8 T cells, with reduced trafficking of these populations to pancreatic lymph nodes. It is also possible that the SDF-1 peptide agonist may enhance stimulation of chemorepulsion effects by Slit-2 agonists.

The present invention may be used for vertebrates generally, and for mammals particularly, and more particularly for humans or for companion animals such as dogs, cats, and horses.

The complete disclosures of all references cited in the specification are hereby incorporated by reference in their entirety, as is the complete disclosure of priority application Ser. No. 61/700,429. In the event of an otherwise irresolvable conflict, however, the disclosure of the present specification shall control.

What is claimed:

1. A method for treating one of insulitis and autoimmune diabetes in a vertebrate patient in need thereof, said method comprising the steps of:
   assaying CD3 T cells from the patient for a level of expression of a marker, where the marker is one of C-X-C chemokine receptor type 4 (CXCR4), roundabout axon guidance receptor homolog 1 (ROBO1), and both CXCR4 and ROBO1;
   conducting the assay by one of
      detecting whether CXCR4 is present in the CD3 T cells sample by contacting the CD3 T cells sample with an anti-CXCR4-1 antibody and detecting binding between anti-CXCR4 antibody and
      detecting whether ROBO1 is present in the CD3 T cells sample by contacting the CD3 T cells sample with an anti-ROBO1 antibody and detecting binding between anti-ROBO1 antibody;
   comparing the patient marker expression level with a mean marker level for non-diabetic, conspecific individuals;
   identifying the patient as having autoimmune diabetes or insulitis when the marker expression level is higher than the non-diabetic mean level at a significance level of p<0.05; and administering a therapeutic for autoimmune diabetes or insulitis to the patient when the patient is thus identified as having autoimmune diabetes or insulitis;

wherein the therapeutic includes an SDF-1 agonist.

2. The method of claim 1, wherein the marker is CXCR4.

3. The method of claim 1, wherein the marker is ROBO1.

4. The method of claim 1, wherein the marker is both CXCR4 and ROBO1.

5. The method of claim 1, wherein the CD3 T cells are peripheral CD3 T cells.

6. The method of claim 1, wherein said marker is one of CXCR4 protein, ROBO1 protein, and both CXCR4 protein and ROBO1 protein.

7. The method of claim 1, wherein the marker is one of CXCR4 mRNA, ROBO1 mRNA, and both CXCR4 mRNA and ROBO1 mRNA.

8. The method of claim 1, further comprising the step of assaying at least one additional biomarker associated with one of insulitis and autoimmune diabetes, wherein the at least one additional biomarker does not include CXCR4 and ROBO1.

9. The method of claim 1, further comprising the step of assaying patient T cells for the marker expression level on at least one additional date to monitor a temporal progression of autoimmune diabetes.

10. The method of claim 1, further comprising the step of assaying CD4 T cells from a patient for levels of expression of the marker.

11. The method of claim 1, further comprising the step of assaying CD8 T cells from a patient for levels of expression of the marker.

12. The method of claim 1, further comprising the step of identifying a disease duration based on levels of ROBO1 and CXCR4.

13. The method of claim 1, further comprising the step of identifying a disease duration based on levels of ROBO1.

14. A method for treating one of insulitis and autoimmune diabetes in a vertebrate patient in need thereof, said method comprising the steps of:

assaying T cells from the patient for a level of expression of a marker, where the marker is one of C-X-C chemokine receptor type 4 (CXCR4), roundabout axon guidance receptor homolog 1 (ROBO1), and both CXCR4 and ROBO1;

comparing the patient marker expression level with a mean marker level for non-diabetic, conspecific individuals;

identifying the patient as having autoimmune diabetes or insulitis when the marker expression level is at least twice as high as a non-diabetic mean level; and administering a therapeutic for autoimmune diabetes or insulitis to the patient when the patient is thus identified as having autoimmune diabetes or insulitus;

wherein the therapeutic includes an SDF-1 agonist.

15. The method of claim 14, wherein the SDF-1 agonist is CTCE-0214.

16. The method of claim 14, wherein the marker is CXCR4.

17. The method of claim 14, wherein the marker is ROBO1.

18. The method of claim 14, wherein the marker is both CXCR4 and ROBO1.

* * * * *

SEQUENCE LISTING

```
<160> NUMBER OF SEQ ID NOS: 43

<210> SEQ ID NO 1
<211> LENGTH: 9
<212> TYPE: PRT
<213> ORGANISM: Artificial sequence
<220> FEATURE:
<223> OTHER INFORMATION: SDF-1 peptide mimetic

<400> SEQUENCE: 1

Ala Tyr Trp Lys Glu Asn Lys Glu Gln
```

<210> SEQ ID NO 2
<211> LENGTH: 28
<212> TYPE: PRT
<213> ORGANISM: Artificial sequence
<220> FEATURE:
<223> OTHER INFORMATION: CTCE-0214 peptide mimetic.
<220> FEATURE:
<221> NAME/KEY: misc_feature
<222> LOCATION: (15)..(15)
<223> OTHER INFORMATION: Xaa is a linker
<220> FEATURE:
<221> NAME/KEY: misc_feature
<222> LOCATION: (28)..(28)
<223> OTHER INFORMATION: Xaa is Asn-OH

<400> SEQUENCE: 2

Lys Pro Val Ser Leu Ser Tyr Arg Cys Pro Cys Arg Phe Phe Xaa Leu
1               5                   10                  15

Lys Trp Ile Gln Glu Tyr Leu Glu Lys Ala Leu Xaa
            20                  25

<210> SEQ ID NO 3
<211> LENGTH: 217
<212> TYPE: PRT
<213> ORGANISM: Homo sapiens
<220> FEATURE:
<221> NAME/KEY: misc_feature
<223> OTHER INFORMATION: LRR Domain 2

<400> SEQUENCE: 3

Met Ala Pro Ser Cys Ser Val Leu His Cys Pro Ala Ala Cys Thr Cys
1               5                   10                  15

Ser Asn Asn Ile Val Asp Cys Arg Gly Lys Gly Leu Thr Glu Ile Pro
            20                  25                  30

Thr Asn Leu Pro Glu Thr Ile Thr Glu Ile Arg Leu Glu Gln Asn Thr
        35                  40                  45

Ile Lys Val Ile Pro Pro Gly Ala Phe Ser Pro Tyr Lys Lys Leu Arg
    50                  55                  60

Arg Ile Asp Leu Ser Asn Asn Gln Ile Ser Glu Leu Ala Pro Asp Ala
65                  70                  75                  80

Phe Gln Gly Leu Arg Ser Leu Asn Ser Leu Val Leu Tyr Gly Asn Lys
                85                  90                  95

Ile Thr Glu Leu Pro Lys Ser Leu Phe Glu Gly Leu Phe Ser Leu Gln
            100                 105                 110

Leu Leu Leu Leu Asn Ala Asn Lys Ile Asn Cys Leu Arg Val Asp Ala
        115                 120                 125

Phe Gln Asp Leu His Asn Leu Asn Leu Leu Ser Leu Tyr Asp Asn Lys
    130                 135                 140

Leu Gln Thr Ile Ala Lys Gly Thr Phe Ser Pro Leu Arg Ala Ile Gln
145                 150                 155                 160

Thr Met His Leu Ala Gln Asn Pro Phe Ile Cys Asp Cys His Leu Lys
                165                 170                 175

Trp Leu Ala Asp Tyr Leu His Thr Asn Pro Ile Glu Thr Ser Gly Ala
            180                 185                 190

Arg Cys Thr Ser Pro Arg Arg Leu Ala Asn Lys Arg Ile Gly Gln Ile
        195                 200                 205

Lys Ser Lys Lys Phe Arg Cys Ser Ala
    210                 215

```
<210> SEQ ID NO 4
<211> LENGTH: 22
<212> TYPE: PRT
<213> ORGANISM: Homo sapiens
<220> FEATURE:
<221> NAME/KEY: misc_feature
<223> OTHER INFORMATION: LRR 1

<400> SEQUENCE: 4

Asn Thr Glu Arg Leu Asp Leu Asn Gly Asn Asn Ile Thr Arg Ile Thr
1               5                   10                  15

Lys Thr Asp Phe Ala Gly
            20

<210> SEQ ID NO 5
<211> LENGTH: 22
<212> TYPE: PRT
<213> ORGANISM: Homo sapiens
<220> FEATURE:
<221> NAME/KEY: misc_feature
<223> OTHER INFORMATION: LRR 2

<400> SEQUENCE: 5

His Leu Arg Val Leu Gln Leu Met Glu Asn Lys Ile Ser Thr Ile Glu
1               5                   10                  15

Arg Gly Ala Phe Gln Asp
            20

<210> SEQ ID NO 6
<211> LENGTH: 22
<212> TYPE: PRT
<213> ORGANISM: Homo sapiens
<220> FEATURE:
<221> NAME/KEY: misc_feature
<223> OTHER INFORMATION: LRR 3

<400> SEQUENCE: 6

Glu Leu Glu Arg Leu Arg Leu Asn Arg Asn His Leu Gln Leu Phe Pro
1               5                   10                  15

Glu Leu Leu Phe Leu Gly
            20

<210> SEQ ID NO 7
<211> LENGTH: 22
<212> TYPE: PRT
<213> ORGANISM: Homo sapiens
<220> FEATURE:
<221> NAME/KEY: misc_feature
<223> OTHER INFORMATION: LRR 4

<400> SEQUENCE: 7

Thr Ile Thr Glu Ile Arg Leu Glu Gln Asn Thr Ile Lys Val Ile Pro
1               5                   10                  15

Pro Gly Ala Phe Ser Pro
            20

<210> SEQ ID NO 8
<211> LENGTH: 22
<212> TYPE: PRT
<213> ORGANISM: Homo sapiens
<220> FEATURE:
<221> NAME/KEY: misc_feature
<223> OTHER INFORMATION: LRR 5

<400> SEQUENCE: 8
```

Lys Leu Arg Arg Ile Asp Leu Ser Asn Asn Gln Ile Ser Glu Leu Ala
1               5                   10                  15

Pro Asp Ala Phe Gln Gly
            20

<210> SEQ ID NO 9
<211> LENGTH: 22
<212> TYPE: PRT
<213> ORGANISM: Homo sapiens
<220> FEATURE:
<221> NAME/KEY: misc_feature
<223> OTHER INFORMATION: LRR 6

<400> SEQUENCE: 9

Asp Leu Glu Val Leu Thr Leu Asn Asn Asn Ile Thr Arg Leu Ser
1               5                   10                  15

Val Ala Ser Phe Asn His
            20

<210> SEQ ID NO 10
<211> LENGTH: 22
<212> TYPE: PRT
<213> ORGANISM: Homo sapiens
<220> FEATURE:
<221> NAME/KEY: misc_feature
<223> OTHER INFORMATION: LRR 7

<400> SEQUENCE: 10

Thr Ile Thr Glu Ile Arg Leu Glu Gln Asn Thr Ile Lys Val Ile Pro
1               5                   10                  15

Pro Gly Ala Phe Ser Pro
            20

<210> SEQ ID NO 11
<211> LENGTH: 22
<212> TYPE: PRT
<213> ORGANISM: Homo sapiens
<220> FEATURE:
<221> NAME/KEY: misc_feature
<223> OTHER INFORMATION: LRR 8

<400> SEQUENCE: 11

Lys Leu Arg Arg Ile Asp Leu Ser Asn Asn Gln Ile Ser Glu Leu Ala
1               5                   10                  15

Pro Asp Ala Phe Gln Gly
            20

<210> SEQ ID NO 12
<211> LENGTH: 22
<212> TYPE: PRT
<213> ORGANISM: Homo sapiens
<220> FEATURE:
<221> NAME/KEY: misc_feature
<223> OTHER INFORMATION: LRR 9

<400> SEQUENCE: 12

Ser Leu Asn Ser Leu Val Leu Tyr Gly Asn Lys Ile Thr Glu Leu Pro
1               5                   10                  15

Lys Ser Leu Phe Glu Gly
            20

<210> SEQ ID NO 13
<211> LENGTH: 22
<212> TYPE: PRT
<213> ORGANISM: Homo sapiens

```
<220> FEATURE:
<221> NAME/KEY: misc_feature
<223> OTHER INFORMATION: LRR 10

<400> SEQUENCE: 13

Ser Leu Gln Leu Leu Leu Leu Asn Ala Asn Lys Ile Asn Cys Leu Arg
1               5                   10                  15

Val Asp Ala Phe Gln Asp
            20

<210> SEQ ID NO 14
<211> LENGTH: 22
<212> TYPE: PRT
<213> ORGANISM: Homo sapiens
<220> FEATURE:
<221> NAME/KEY: misc_feature
<223> OTHER INFORMATION: LRR 11

<400> SEQUENCE: 14

Asn Leu Asn Leu Leu Ser Leu Tyr Asp Asn Lys Leu Gln Thr Ile Ala
1               5                   10                  15

Lys Gly Thr Phe Ser Pro
            20

<210> SEQ ID NO 15
<211> LENGTH: 22
<212> TYPE: PRT
<213> ORGANISM: Homo sapiens
<220> FEATURE:
<221> NAME/KEY: misc_feature
<223> OTHER INFORMATION: LRR 12

<400> SEQUENCE: 15

Tyr Thr Ala Glu Leu Arg Leu Asn Asn Asn Glu Phe Thr Val Leu Glu
1               5                   10                  15

Ala Thr Gly Ile Phe Lys
            20

<210> SEQ ID NO 16
<211> LENGTH: 22
<212> TYPE: PRT
<213> ORGANISM: Homo sapiens
<220> FEATURE:
<221> NAME/KEY: misc_feature
<223> OTHER INFORMATION: LRR 13

<400> SEQUENCE: 16

Gln Leu Arg Lys Ile Asn Phe Ser Asn Asn Lys Ile Thr Asp Ile Glu
1               5                   10                  15

Glu Gly Ala Phe Glu Gly
            20

<210> SEQ ID NO 17
<211> LENGTH: 22
<212> TYPE: PRT
<213> ORGANISM: Homo sapiens
<220> FEATURE:
<221> NAME/KEY: misc_feature
<223> OTHER INFORMATION: LRR 14

<400> SEQUENCE: 17

Gly Val Asn Glu Ile Leu Leu Thr Ser Asn Arg Leu Glu Asn Val Gln
1               5                   10                  15

His Lys Met Phe Lys Gly
            20
```

```
<210> SEQ ID NO 18
<211> LENGTH: 22
<212> TYPE: PRT
<213> ORGANISM: Homo sapiens
<220> FEATURE:
<221> NAME/KEY: misc_feature
<223> OTHER INFORMATION: LRR 15

<400> SEQUENCE: 18

Ser Leu Lys Thr Leu Met Leu Arg Ser Asn Arg Ile Thr Cys Val Gly
1               5                   10                  15

Asn Asp Ser Phe Ile Gly
            20

<210> SEQ ID NO 19
<211> LENGTH: 22
<212> TYPE: PRT
<213> ORGANISM: Homo sapiens
<220> FEATURE:
<221> NAME/KEY: misc_feature
<223> OTHER INFORMATION: LRR 16

<400> SEQUENCE: 19

Ser Val Arg Leu Leu Ser Leu Tyr Asp Asn Gln Ile Thr Thr Val Ala
1               5                   10                  15

Pro Gly Ala Phe Asp Thr
            20

<210> SEQ ID NO 20
<211> LENGTH: 23
<212> TYPE: PRT
<213> ORGANISM: Homo sapiens
<220> FEATURE:
<221> NAME/KEY: misc_feature
<223> OTHER INFORMATION: LRR 17

<400> SEQUENCE: 20

Asp Val Thr Glu Leu Tyr Leu Asp Gly Asn Gln Phe Thr Leu Val Pro
1               5                   10                  15

Lys Glu Leu Ser Asn Tyr Lys
            20

<210> SEQ ID NO 21
<211> LENGTH: 22
<212> TYPE: PRT
<213> ORGANISM: Homo sapiens
<220> FEATURE:
<221> NAME/KEY: misc_feature
<223> OTHER INFORMATION: LRR 18

<400> SEQUENCE: 21

His Leu Thr Leu Ile Asp Leu Ser Asn Asn Arg Ile Ser Thr Leu Ser
1               5                   10                  15

Asn Gln Ser Phe Ser Asn
            20

<210> SEQ ID NO 22
<211> LENGTH: 22
<212> TYPE: PRT
<213> ORGANISM: Homo sapiens
<220> FEATURE:
<221> NAME/KEY: misc_feature
<223> OTHER INFORMATION: LRR 19

<400> SEQUENCE: 22
```

Gln Leu Leu Thr Leu Ile Leu Ser Tyr Asn Arg Leu Arg Cys Ile Pro
1               5                   10                  15

Pro Arg Thr Phe Asp Gly
            20

<210> SEQ ID NO 23
<211> LENGTH: 22
<212> TYPE: PRT
<213> ORGANISM: Homo sapiens
<220> FEATURE:
<221> NAME/KEY: misc_feature
<223> OTHER INFORMATION: LRR 20

<400> SEQUENCE: 23

Ser Leu Arg Leu Leu Ser Leu His Gly Asn Asp Ile Ser Val Val Pro
1               5                   10                  15

Glu Gly Ala Phe Asn Asp
            20

<210> SEQ ID NO 24
<211> LENGTH: 9
<212> TYPE: PRT
<213> ORGANISM: Homo sapiens
<220> FEATURE:
<221> NAME/KEY: misc_feature
<223> OTHER INFORMATION: LRR 1 core

<400> SEQUENCE: 24

Thr Glu Arg Leu Asp Leu Asn Gly Asn
1               5

<210> SEQ ID NO 25
<211> LENGTH: 9
<212> TYPE: PRT
<213> ORGANISM: Homo sapiens
<220> FEATURE:
<221> NAME/KEY: misc_feature
<223> OTHER INFORMATION: LRR 2 core

<400> SEQUENCE: 25

Leu Arg Val Leu Gln Leu Met Glu Asn
1               5

<210> SEQ ID NO 26
<211> LENGTH: 9
<212> TYPE: PRT
<213> ORGANISM: Homo sapiens
<220> FEATURE:
<221> NAME/KEY: misc_feature
<223> OTHER INFORMATION: LRR 3 core

<400> SEQUENCE: 26

Leu Glu Arg Leu Arg Leu Asn Arg Asn
1               5

<210> SEQ ID NO 27
<211> LENGTH: 9
<212> TYPE: PRT
<213> ORGANISM: Homo sapiens
<220> FEATURE:
<221> NAME/KEY: misc_feature
<223> OTHER INFORMATION: LRR 4 core

<400> SEQUENCE: 27

Leu Tyr Arg Leu Asp Leu Ser Glu Asn
1               5

<210> SEQ ID NO 28
<211> LENGTH: 9
<212> TYPE: PRT
<213> ORGANISM: Homo sapiens
<220> FEATURE:
<221> NAME/KEY: misc_feature
<223> OTHER INFORMATION: LRR 5 core

<400> SEQUENCE: 28

Ile Lys Asn Leu Gln Leu Asp Tyr Asn
1               5

<210> SEQ ID NO 29
<211> LENGTH: 9
<212> TYPE: PRT
<213> ORGANISM: Homo sapiens
<220> FEATURE:
<221> NAME/KEY: misc_feature
<223> OTHER INFORMATION: LRR 6 core

<400> SEQUENCE: 29

Leu Glu Val Leu Thr Leu Asn Asn Asn
1               5

<210> SEQ ID NO 30
<211> LENGTH: 9
<212> TYPE: PRT
<213> ORGANISM: Homo sapiens
<220> FEATURE:
<221> NAME/KEY: misc_feature
<223> OTHER INFORMATION: LRR 7 core

<400> SEQUENCE: 30

Ile Thr Glu Ile Arg Leu Glu Gln Asn
1               5

<210> SEQ ID NO 31
<211> LENGTH: 9
<212> TYPE: PRT
<213> ORGANISM: Homo sapiens
<220> FEATURE:
<221> NAME/KEY: misc_feature
<223> OTHER INFORMATION: LRR 8 core

<400> SEQUENCE: 31

Leu Arg Arg Ile Asp Leu Ser Asn Asn
1               5

<210> SEQ ID NO 32
<211> LENGTH: 9
<212> TYPE: PRT
<213> ORGANISM: Homo sapiens
<220> FEATURE:
<221> NAME/KEY: misc_feature
<223> OTHER INFORMATION: LRR 9 core

<400> SEQUENCE: 32

Leu Asn Ser Leu Val Leu Tyr Gly Asn
1               5

<210> SEQ ID NO 33
<211> LENGTH: 9
<212> TYPE: PRT
<213> ORGANISM: Homo sapiens
<220> FEATURE:
<221> NAME/KEY: misc_feature
<223> OTHER INFORMATION: LRR 10 core

<400> SEQUENCE: 33

Leu Gln Leu Leu Leu Asn Ala Asn
1               5

<210> SEQ ID NO 34
<211> LENGTH: 9
<212> TYPE: PRT
<213> ORGANISM: Homo sapiens
<220> FEATURE:
<221> NAME/KEY: misc_feature
<223> OTHER INFORMATION: LRR 11 core

<400> SEQUENCE: 34

Leu Asn Leu Leu Ser Leu Tyr Asp Asn
1               5

<210> SEQ ID NO 35
<211> LENGTH: 9
<212> TYPE: PRT
<213> ORGANISM: Homo sapiens
<220> FEATURE:
<221> NAME/KEY: misc_feature
<223> OTHER INFORMATION: LRR 12 core

<400> SEQUENCE: 35

Thr Ala Glu Leu Arg Leu Asn Asn
1               5

<210> SEQ ID NO 36
<211> LENGTH: 9
<212> TYPE: PRT
<213> ORGANISM: Homo sapiens
<220> FEATURE:
<221> NAME/KEY: misc_feature
<223> OTHER INFORMATION: LRR 13 core

<400> SEQUENCE: 36

Leu Arg Lys Ile Asn Phe Ser Asn Asn
1               5

<210> SEQ ID NO 37
<211> LENGTH: 9
<212> TYPE: PRT
<213> ORGANISM: Homo sapiens
<220> FEATURE:
<221> NAME/KEY: misc_feature
<223> OTHER INFORMATION: LRR 14 core

<400> SEQUENCE: 37

Val Asn Glu Ile Leu Leu Thr Ser Asn
1               5

<210> SEQ ID NO 38
<211> LENGTH: 9
<212> TYPE: PRT
<213> ORGANISM: Homo sapiens
<220> FEATURE:
<221> NAME/KEY: misc_feature
<223> OTHER INFORMATION: LRR 15 core

<400> SEQUENCE: 38

Leu Lys Thr Leu Met Leu Arg Ser Asn
1               5

<210> SEQ ID NO 39
<211> LENGTH: 9

```
<212> TYPE: PRT
<213> ORGANISM: Homo sapiens
<220> FEATURE:
<221> NAME/KEY: misc_feature
<223> OTHER INFORMATION: LRR 16 core

<400> SEQUENCE: 39

Val Arg Leu Leu Ser Leu Tyr Asp Asn
1               5

<210> SEQ ID NO 40
<211> LENGTH: 9
<212> TYPE: PRT
<213> ORGANISM: Homo sapiens
<220> FEATURE:
<221> NAME/KEY: misc_feature
<223> OTHER INFORMATION: LRR 17 core

<400> SEQUENCE: 40

Val Thr Glu Leu Tyr Leu Asp Gly Asn
1               5

<210> SEQ ID NO 41
<211> LENGTH: 9
<212> TYPE: PRT
<213> ORGANISM: Homo sapiens
<220> FEATURE:
<221> NAME/KEY: misc_feature
<223> OTHER INFORMATION: LRR 18 core

<400> SEQUENCE: 41

Leu Thr Leu Ile Asp Leu Ser Asn Asn
1               5

<210> SEQ ID NO 42
<211> LENGTH: 9
<212> TYPE: PRT
<213> ORGANISM: Homo sapiens
<220> FEATURE:
<221> NAME/KEY: misc_feature
<223> OTHER INFORMATION: LRR 19 core

<400> SEQUENCE: 42

Leu Leu Thr Leu Ile Leu Ser Tyr Asn
1               5

<210> SEQ ID NO 43
<211> LENGTH: 9
<212> TYPE: PRT
<213> ORGANISM: Homo sapiens
<220> FEATURE:
<221> NAME/KEY: misc_feature
<223> OTHER INFORMATION: LRR 20 core

<400> SEQUENCE: 43

Leu Arg Leu Leu Ser Leu His Gly Asn
1               5
```